US009493752B2

(12) United States Patent
Collin et al.

(10) Patent No.: US 9,493,752 B2
(45) Date of Patent: Nov. 15, 2016

(54) **ENDOGLYCOSIDASE FROM *STREPTOCOCCUS PYOGENES* AND METHODS USING IT**

(75) Inventors: Mattias Collin, Lund (SE); Maria Allhorn, Lund (SE); Jonathan Sjögren, Lund (SE)

(73) Assignee: Genovis AB, Lund (SE)

( * ) Notice: Subject to any disclaimer, the term of this patent is extended or adjusted under 35 U.S.C. 154(b) by 252 days.

(21) Appl. No.: 14/343,938

(22) PCT Filed: Sep. 12, 2012

(86) PCT No.: PCT/EP2012/067841
§ 371 (c)(1),
(2), (4) Date: Jun. 16, 2014

(87) PCT Pub. No.: WO2013/037824
PCT Pub. Date: Mar. 21, 2013

(65) Prior Publication Data
US 2014/0302519 A1 Oct. 9, 2014

(30) Foreign Application Priority Data

Sep. 13, 2011 (SE) ...................................... 1115841

(51) Int. Cl.
*G01N 33/68* (2006.01)
*C12N 9/24* (2006.01)
(Continued)

(52) U.S. Cl.
CPC ........... *C12N 9/2405* (2013.01); *C12N 9/2402* (2013.01); *C12P 21/005* (2013.01);
(Continued)

(58) Field of Classification Search
CPC ........... C12N 9/2405; G01N 33/6845; G01N 2469/20; C12Q 1/34; C12Q 1/37; C07K 2317/41; C12P 21/005
See application file for complete search history.

(56) References Cited

U.S. PATENT DOCUMENTS

| 8,889,128 B2 * | 11/2014 | Bjorck | A61K 38/47 424/190.1 |
| 2010/0135981 A1 * | 6/2010 | Bjorck | A61K 48/005 424/94.61 |
| 2012/0196310 A1 * | 8/2012 | Jaeger | C12Q 1/37 435/23 |

FOREIGN PATENT DOCUMENTS

| WO | WO-03/051914 | 6/2003 |
| WO | WO-2008/071418 | 6/2008 |

(Continued)

OTHER PUBLICATIONS

Allhorn et al., "EndoS from *Streptococcus pyogenes* is hydrolyzed by the cystein proteinase SpeB and requires glutamic acid 235 and tryptophans for IgG glycan-hydrolyzing activity", BMC Microbiology (2008) 8(3):1-10.

(Continued)

*Primary Examiner* — Nashaat Nashed
*Assistant Examiner* — William W Moore
(74) *Attorney, Agent, or Firm* — Morrison & Foerster LLP

(57) ABSTRACT

The invention provides an endoglycosidase, referred to as EndoS49 and having the amino acid sequence of SEQ ID NO: 1. EndoS49 was isolated from *Streptococcus pyogenes* strain NZ131 and is a homolog of EndoS. EndoS49 has specific endoglycosidase activity on native IgG and cleaves a larger variety of Fc glycans than EndoS. A mutant thereof where the glutamic acid at position 186 of SEQ ID NO: 1 was substituted was produced: said mutant lacks endoglycosidase activity but is capable of binding to IgG. Methods using EndoS49, deletions thereof and said mutant, especially for assessing glycosylation of IgG or for isolating IgG are disclosed.

3 Claims, 4 Drawing Sheets

(51) Int. Cl.
  *G01N 33/569* (2006.01)
  *C12P 21/00* (2006.01)
  *C12Q 1/34* (2006.01)
  *C12Q 1/37* (2006.01)

(52) U.S. Cl.
  CPC .............. *C12Q 1/34* (2013.01); *C12Q 1/37* (2013.01); *C12Y 302/01096* (2013.01); *G01N 33/56944* (2013.01); *G01N 33/6854* (2013.01); *C07K 2317/41* (2013.01); *G01N 2469/20* (2013.01)

(56) References Cited

FOREIGN PATENT DOCUMENTS

| WO | WO-2009/033670 | 3/2009 |
|----|----------------|--------|
| WO | WO-2010/057626 | 5/2010 |

OTHER PUBLICATIONS

Allhorn and Collin., "Sugar-free Antibodies—The Bacterial Solution to Autoimmunity?", Contemporary Challenges in Autoimmunity: Ann. N.Y. Acad. Sci. (2009) 1173:664-669.

Collin and Olsen, "EndoS, a novel secreted protein from *Streptococcus pyogenes* with endoglycosidase activity on human IgG", The EMBO Journal (2001) 20(12):3046-3055.

Database EMBL, accession No. EM_STD: CP000829, "*Streptococcus pyogens* NZ131, complete genome", Oct. 18, 2008.

Database Uniprot, accession No. Uniprot: B5XI26, "SubName: Secreted Endo-beta-N-acetylglucosaminidase(EndoS)", Nov. 25, 2008.

International Search Report and Written Opinion for PCT/EP2012/067841, mailed Nov. 23, 2012, 16 pages.

McShan et al., "Genome Sequence of a Nephritogenic and Highly Transformable M49 Strain of *Streptococcus pyogenes*", Journal of Bacteriology (2008) 190(23):7773-7785.

\* cited by examiner

Figure 1.

Figure 2.
A EndoS49 IgG activity
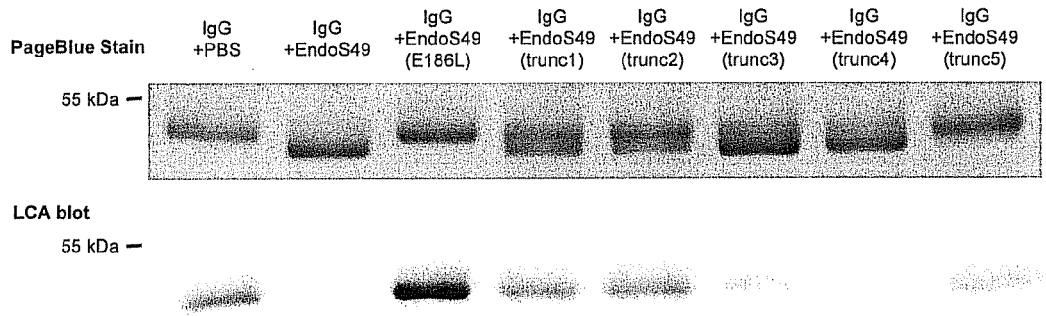
B EndoS49 activity on IgG subclasses
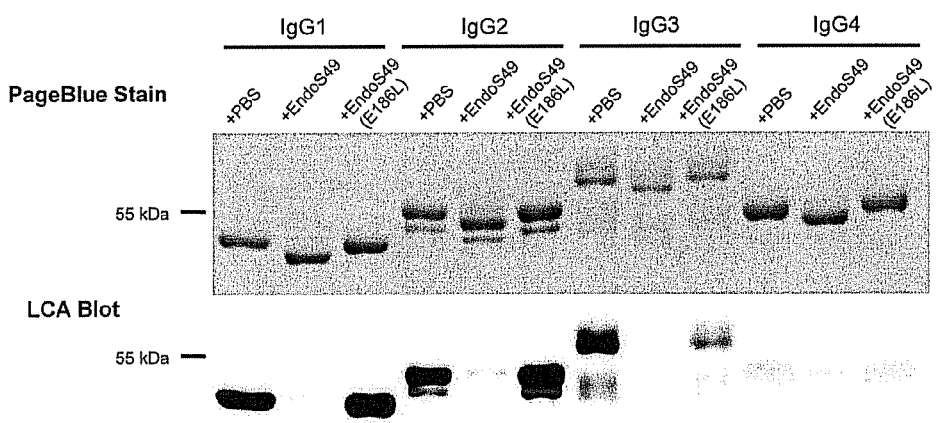
C EndoS49 Alpha-1-microglobulin (A1m) activity
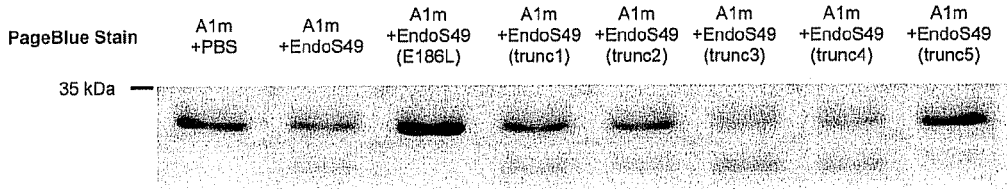

Figure 5. Phylogenetic tree of endoglycosidases
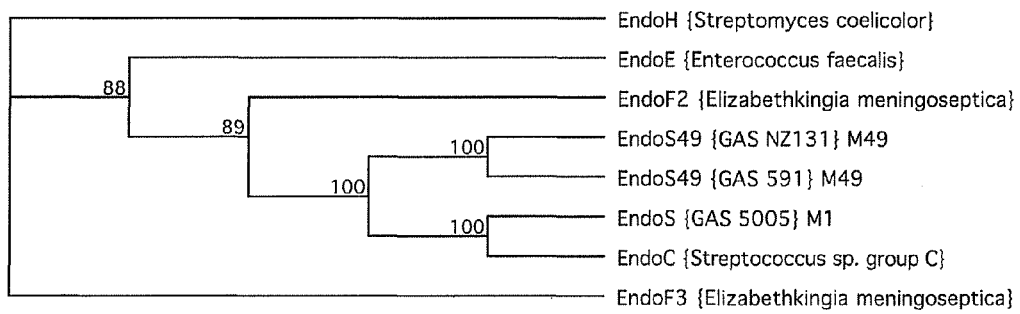
Figure 6.
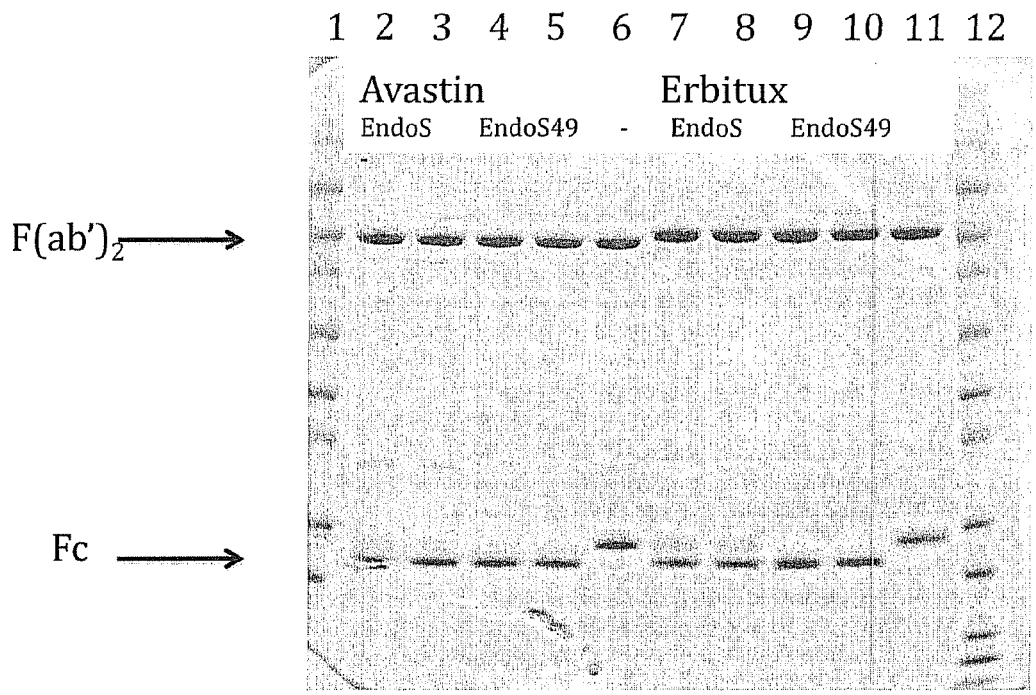

SEQUENCE LISTING

```
<160> NUMBER OF SEQ ID NOS: 19

<210> SEQ ID NO 1
<211> LENGTH: 843
<212> TYPE: PRT
<213> ORGANISM: Streptococcus pyogenes

<400> SEQUENCE: 1

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45
```

```
Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
                180                 185                 190

Arg Thr Pro Glu Glu Asp Ala Arg Ala Leu Asn Val Phe Lys Glu Ile
                195                 200                 205

Ala Gln Leu Ile Gly Lys Asn Gly Ser Asp Lys Ser Lys Leu Leu Ile
210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
                260                 265                 270

Asn Tyr Ile Asp Ala Ser Gln Phe Met Ile Gly Phe Ser Phe Phe Glu
            275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
            355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
    435                 440                 445

Leu Arg Gln Leu Ser Asn Val Lys Glu Ile Thr Pro Glu Leu Leu Pro
450                 455                 460
```

```
Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
            485                 490                 495

Ile Asp Val Asn Ser Ile Thr His Leu Thr Ser Phe Asp Ile Ser His
        500                 505                 510

Asn Ser Leu Asp Leu Ser Glu Lys Ser Glu Asp Arg Lys Leu Leu Met
    515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
    610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Asp Glu Thr Tyr Leu Val Asp
                645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
    690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
    770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
        835                 840

<210> SEQ ID NO 2
<211> LENGTH: 843
<212> TYPE: PRT
<213> ORGANISM: Streptococcus pyogenes
```

```
<400> SEQUENCE: 2

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Leu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415
```

-continued

```
Asp Leu Glu Arg Tyr Asn Lys Thr Leu Val Leu Thr Gly Asp Lys Ile
            420                 425                 430
Gln Asn Leu Lys Gly Leu Glu Lys Leu Ser Lys Leu Gln Lys Leu Glu
            435                 440                 445
Leu Arg Gln Leu Ser Asn Val Lys Glu Ile Thr Pro Glu Leu Leu Pro
            450                 455                 460
Glu Ser Met Lys Lys Asp Ala Glu Leu Val Met Val Gly Met Thr Gly
465                 470                 475                 480
Leu Glu Lys Leu Asn Leu Ser Gly Leu Asn Arg Gln Thr Leu Asp Gly
            485                 490                 495
Ile Asp Val Asn Ser Ile Thr His Leu Thr Ser Phe Asp Ile Ser His
            500                 505                 510
Asn Ser Leu Asp Leu Ser Glu Lys Ser Glu Asp Arg Lys Leu Leu Met
            515                 520                 525
Thr Leu Met Glu Gln Val Ser Asn His Gln Lys Ile Thr Val Lys Asn
            530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
            565                 570                 575
Leu Thr Asp Phe Val Phe Gly Thr Val Thr Lys Arg Asn Thr Phe Ile
            580                 585                 590
Gly Asp Glu Glu Ala Phe Ala Ile Tyr Lys Glu Gly Ala Val Asp Gly
            595                 600                 605
Arg Gln Tyr Val Ser Lys Asp Tyr Thr Tyr Glu Ala Phe Arg Lys Asp
            610                 615                 620
Tyr Lys Gly Tyr Lys Val His Leu Thr Ala Ser Asn Leu Gly Glu Thr
625                 630                 635                 640
Val Thr Ser Lys Val Thr Ala Thr Thr Asp Glu Thr Tyr Leu Val Asp
            645                 650                 655
Val Ser Asp Gly Glu Lys Val Val His His Met Lys Leu Asn Ile Gly
            660                 665                 670
Ser Gly Ala Ile Met Met Glu Asn Leu Ala Lys Gly Ala Lys Val Ile
            675                 680                 685
Gly Thr Ser Gly Asp Phe Glu Gln Ala Lys Lys Ile Phe Asp Gly Glu
            690                 695                 700
Lys Ser Asp Arg Phe Phe Thr Trp Gly Gln Thr Asn Trp Ile Ala Phe
705                 710                 715                 720
Asp Leu Gly Glu Ile Asn Leu Ala Lys Glu Trp Arg Leu Phe Asn Ala
            725                 730                 735
Glu Thr Asn Thr Glu Ile Lys Thr Asp Ser Ser Leu Asn Val Ala Lys
            740                 745                 750
Gly Arg Leu Gln Ile Leu Lys Asp Thr Thr Ile Asp Leu Glu Lys Met
            755                 760                 765
Asp Ile Lys Asn Arg Lys Glu Tyr Leu Ser Asn Asp Glu Asn Trp Thr
            770                 775                 780
Asp Val Ala Gln Met Asp Asp Ala Lys Ala Ile Phe Asn Ser Lys Leu
785                 790                 795                 800
Ser Asn Val Leu Ser Arg Tyr Trp Arg Phe Cys Val Asp Gly Gly Ala
            805                 810                 815
```

| Ser | Ser | Tyr | Tyr | Pro | Gln | Tyr | Thr | Glu | Leu | Gln | Ile | Leu | Gly | Gln | Arg |
|-----|-----|-----|-----|-----|-----|-----|-----|-----|-----|-----|-----|-----|-----|-----|-----|
|     |     | 820 |     |     |     | 825 |     |     |     |     | 830 |     |     |     |     |

| Leu | Ser | Asn | Asp | Val | Ala | Asn | Thr | Leu | Lys | Asp |
|-----|-----|-----|-----|-----|-----|-----|-----|-----|-----|-----|
|     | 835 |     |     |     | 840 |     |     |     |     |     |

<210> SEQ ID NO 3
<211> LENGTH: 2532
<212> TYPE: DNA
<213> ORGANISM: Streptococcus pyogenes

<400> SEQUENCE: 3

```
atggataaac atttgttggt aaaaagaaca ctagggtgtg tttgtgctgc aacgttgatg      60
ggagctgcct tagcgaccca ccatgattca ctcaatactg taaaagcgga ggagaagact     120
gttcaaacag aaagacagat cagcaggtt ggtgctaaat ggtacagga atccgtgaa        180
ggaaaacgcg gaccactata tgctggttat tttaggacat ggcatgatcg tgcttcaaca     240
ggaatagatg gtaaacagca acatccagaa atactatgg ctgaggtccc aaaagaagtt     300
gatatcttat ttgtttttca tgaccataca gcttcagata gtccattttg gtctgaatta    360
aaggacagtt atgtccataa attacatcaa cagggaacgg cacttgttca gacaattggt    420
gttaacgaat taaatggacg tacaggttta tctaaagatt atcctgatac tcctgagggg    480
aacaaagctt tagcagcagc cattgtcaag gcatttgtaa ctgatcgtgg tgtcgatgga    540
ctagatattg atattgagca cgaatttacg aacaaaagaa cacctgaaga gatgctcgt    600
gctctaaatg ttttttaaga gattgcgcag ttaataggta aaaatggtag tgataaatct    660
aaattgctca tcatggacac tacccctaagt gttgaaaata atccaatatt taaagggata    720
gcggaagatc ttgattatct tcttagacaa tattatggtt cacaaggtgg agaagctgaa    780
gtggatacta taaactctga ttggaaccaa tatcagaatt atattgatgc tagccagttc    840
atgattggat tctccttttt tgaagaatct gcgtccaaag ggaatttatg gtttgatgtt    900
aacgaatacg accctaacaa tcctgaaaaa gggaaagata ttgaaggaac acgtgctaaa    960
aaatatgcag agtggcaacc tagtacaggt ggtttaaaag caggtatatt ctcttatgct   1020
attgatcgtg atggagtggc tcatgttcct caacatata aaaataggac tagtacaaat    1080
ttacaacggc atgaagtcga taatatctca catactgact acaccgtatc tcgaaaatta   1140
aaaacattga tgaccgaaga caacgctat gatgtcattg atcaaaaaga cattcctgac   1200
ccagcattaa gagaacaaat cattcaacaa gttggacagt ataaggcga tttggaacgt    1260
tataacaaga cattggtgct acaggagat aagattcaaa atcttaaagg actagaaaaa    1320
ttaagcaagt tacaaaaatt agagttgcgc cagctatcta acgttaaaga aattactcca    1380
gaacttttgc cggaaagcat gaaaaagat gctgagcttg ttatggtagg catgactggt    1440
ttagaaaaac taaaccttag tggtctaaat cgtcaaactt agacggtat agacgtgaat    1500
agtattacgc atttgacatc atttgatatt tcacataata gtttggactt gtcggaaaag    1560
agtgaagacc gtaaactatt aatgactttg atggagcagg tttcaaatca tcaaaaaata    1620
acggtgaaaa atacggcttt tgaaaatcaa aaaccgaaag gttattatcc tcagacgtat    1680
gataccaaag aagtcattta tgatgttgat aatgcagaac atgatatttt aactgatttt    1740
gttttttggaa ctgttactaa acgtaatacc tttattggag acgaagaagc atttgctatc    1800
tataaagaag gagctgtcga tggtcgacaa tatgtgtcta agactatac ttatgaagct    1860
tttcgtaaag actataaagg ttacaaggtt catttaactg cttctaacct aggagaaaca    1920
gttacttcta aggtaactgc tactactgat gaaacttact tagtagatgt ttctgatggg   1980
```

-continued

```
gaaaaagttg ttcaccacat gaaactcaat ataggatctg gtgccatcat gatgaaaat      2040 ctggcaaaag gggctaaagt gattggtaca tctggggact ttgagcaagc aaagaagatt      2100
ttcgatggtg aaaagtcaga tagattcttc acttggggac aaactaactg gatagctttt      2160
gatctaggag aaattaatct tgcgaaggaa tggcgtttat ttaatgcaga gacaaatact      2220
gaaataaaga cagatagtag cttaaacgtg gctaaaggac gtcttcagat tttaaaagat      2280
acaactattg atttagaaaa aatggacata aaaaatcgta aagagtatct gtcgaatgat      2340
gaaaattgga ctgatgttgc tcagatggat gatgcaaaag cgatatttaa tagtaaatta      2400
tccaatgttt tatctcggta ttggcggttt tgtgtagatg gtggagctag ctcttattac      2460
cctcaatata ccgaacttca aatcctcgga caacgtttat caaatgatgt cgctaatacg      2520
ctgaaggatt ga                                                          2532
```

<210> SEQ ID NO 4
<211> LENGTH: 310
<212> TYPE: PRT
<213> ORGANISM: Streptococcus pyogenes

<400> SEQUENCE: 4

```
Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

Lys Ile Asn Phe Asn Gly Glu Gln Met Phe Asp Val Lys Glu Ala Ile
            100                 105                 110

Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asp Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Lys Glu Leu Thr Glu Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270
```

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
        290                 295                 300

Ser Trp Asn Gln Thr Asn
305                 310

<210> SEQ ID NO 5
<211> LENGTH: 8
<212> TYPE: PRT
<213> ORGANISM: Artificial Sequence
<220> FEATURE:
<223> OTHER INFORMATION: Cleavage product

<400> SEQUENCE: 5

Gly Pro Ser Val Phe Leu Phe Pro
1               5

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ctgtaaggat ccaggagaag actg                                          24

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
gaaacctcga gtctttgtaa tcgtaggact t                                  31

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
ctagatattg atattcttca cgaatttacg aac                                33

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
gttcgtaaat tcgtgaagaa tatcaatatc tag                                33

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10
atttctcgag ctgaagacgt cctttagcca cg          32

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
taaactcgag ccccatcaga aacatctact aag         33

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
attttctcga ggcattatca acatcataat gacc        34

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
taaactcgag ccagtcatgc ctaccataac aagctcagc   39

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
atttctcgag ctgtccaact tgttgaatg              29

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
aaaacgcgga ccactatatg c                      21

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aaacgttgtc cgaggatttg                        20

```
<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
agcccttgat gatgctttg                                                    19

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
aacaattctg ggtgatcgg                                                    19

<210> SEQ ID NO 19
<211> LENGTH: 8
<212> TYPE: PRT
<213> ORGANISM: Artificial Sequence
<220> FEATURE:
<223> OTHER INFORMATION: GH18 catalytic motif present from residues 179
      to 186 of SEQ ID NO: 1
<220> FEATURE:
<221> NAME/KEY: MISC_FEATURE
<222> LOCATION: (2)..(3)
<223> OTHER INFORMATION: Xaa refers to an unconserved amino acid
<220> FEATURE:
<221> NAME/KEY: MISC_FEATURE
<222> LOCATION: (5)..(5)
<223> OTHER INFORMATION: Xaa refers to an unconserved amino acid
<220> FEATURE:
<221> NAME/KEY: MISC_FEATURE
<222> LOCATION: (7)..(7)
<223> OTHER INFORMATION: Xaa refers to an unconserved amino acid

<400> SEQUENCE: 19

Asp Xaa Xaa Asp Xaa Asp Xaa Glu
1               5
```

ENDOGLYCOSIDASE FROM *STREPTOCOCCUS PYOGENES* AND METHODS USING IT

CROSS-REFERENCE TO RELATED APPLICATIONS

This application is the national phase of PCT application PCT/EP2012/067841 having an international filing date of 12 Sep. 2012, which claims the benefit of British patent application No. 1115841.7 filed 13 Sep. 2011. The contents of the above patent applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 251502010600SeqList.txt, date recorded: Mar. 7, 2014, size: 24,099 bytes).

FIELD OF THE INVENTION

The present invention relates to a novel endoglycosidase, mutants thereof lacking glycan hydrolyzing activity, and its use in methods of hydrolyzing the glycan of glycoproteins.

BACKGROUND OF THE INVENTION

Endoglycosidase S (EndoS) is secreted by a number of serotypes of *Streptococcus pyogenes* and has a specific endoglycosidase activity on native IgG by hydrolyzing the conserved glycans attached to the asparagine 297 residue on the heavy chains of IgG, Collin and Olsen, The EMBO Journal, 2001, 20 3046-3055. EndoS is the first known bacterial enzyme with a unique specificity for native IgG. In contrast, the activities of other known endoglycosidases require or are enhanced by denaturation of the glycoprotein substrate.

Antibodies such as IgG have many applications in basic research as well as in diagnostics and drug development. In some of these applications, such as immunohistochemistry, immunoassays, tumour detection, radiotherapy, crystallographic studies of antibody binding sites and immunotargeting, it is more convenient to use Fab fragments than whole IgG molecules. Some of the advantages of using Fab fragments are that they will not be affected by Fc receptors on cells or precipitate antigen, they display a reduced immunogenicity and are less susceptible to phagocytosis, and that radiolabelled Fab fragments are more rapidly cleared from tissue than whole IgG molecules. For other applications, it is desirable to use Fc fragments of IgG. In further applications, it may be desirable to use deglycosylated versions of the antibodies or other glycoproteins.

The cleavage of IgG into Fab and Fc fragments is most often carried out using proteolytic enzymes such as pepsin or papain. These enzymes often cleave other proteins, so the cleavage reaction generally has to be performed on a purified IgG fraction. Furthermore, pepsin and papain typically cleave IgG in more than one place. This means that the fragments obtained often do not correspond to whole Fab or Fc fragments, and even if cleavage does result in Fab and Fc fragments, they are typically susceptible to further cleavage into smaller fragments. The isolation of Fc fragments from Fab fragments is most often carried out using protein A or G affinity separation columns, which utilise the Fc-binding properties of the bacterial proteins A and G.

Many different glycoproteins have utility in therapeutic applications. Methods to analyse the glycosylation of such proteins have utility in the research and development of the proteins as therapeutics. It may also be desirable to provide deglycosylated versions of these proteins.

SUMMARY OF THE INVENTION

The inventors have identified a novel endoglycosidase from serotype M49 *Streptococcus pyogenes*, referred to herein as EndoS49. EndoS49 was isolated from strain NZ131, a nephritogenic and highly transformable strain of serotype M49. NZ131 strain is a clinical isolate from a case of acute post-streptococcal glomerulonephritis in New Zealand. At a protein level, EndoS49 has less than 40% identity to EndoS, and is a 90 kDa protein, compared to the 108 kDa of EndoS. EndoS49 has deglycosylation activity for a broader range of proteins than EndoS.

The enzyme is a 90 kDa enzyme, having a family 18 glycoside hydrolase catalytic domain. EndoS49 hydrolyzes glycan on human glycoproteins, and in particular IgG1-4, and alpha-1-microglobulin. EndoS49 can be used in the hydrolysis of glycans on human glycoproteins including IgG and alpha-1-microglobulin. EndoS49 can thus be used in glycoprofiling analysis in which the enzyme is contacted with a glycoprotein, and the products produced are separated for analysis of the glycans and the protein. EndoS49 can also be used to prepare deglycosylated proteins. The enzyme can be modified to reduce or remove endoglycosidase activity.

The modified EndoS49 polypeptide which lacks endoglycosidase activity can be used in methods for isolating glycosylated and/or functionally active IgG. By using such a modified EndoS49 polypeptide in combination with an additional IgG-binding reagent which is capable of binding denatured and/or deglycosylated IgG, the inventors have also identified a method for assessing the glycosylation state or functional quality of an IgG-containing sample.

In accordance with the present invention, there is thus provided a polypeptide comprising
  (a) the amino acid sequence of SEQ ID NO: 1;
  (b) a variant thereof having at least 50% identity to the amino acid sequence of SEQ ID NO: 1 and having endogycosidase activity; or
  (c) a fragment of either thereof having endoglycosidase activity.

The invention also provides a polypeptide capable of binding to IgG and which does not have endoglycosidase activity comprising
  (a) the amino acid sequence of SEQ ID NO: 2;
  (b) a variant thereof having at least 50% identity to the amino acid sequence of SEQ ID NO: 1, in which the amino acid equivalent to glutamic acid at position 186 is substituted; or
  (c) a fragment of either thereof.

The invention also provides polynucleotides, expression vectors and host cells encoding or expressing the polypeptides of the invention. The invention also relates to the use of the polypeptides of the invention in a method of determining or analysing the glycosylation state of the protein, and in particular of an antibody, in particular an IgG antibody.

The invention also provides a method for isolating IgG from an IgG-containing sample, which method comprises:

(a) contacting said IgG-containing sample with a modified EndoS49 polypeptide which lacks IgG endoglycosidase activity
(b) separating said EndoS49 from the contacted sample; thereby obtaining isolated IgG.

Additionally there is provided method of assessing the glycosylation state or functional quality of an IgG-containing sample, which method comprises taking a first and a second sub-sample of the IgG-containing sample, and wherein steps (a) and (b) according to the method above are applied to the first sub-sample, and wherein steps (a) and (b) as above are applied to the second sub-sample except the EndoS49 polypeptide is substituted with an alternative IgG-binding reagent which is capable of binding denatured and/or deglycosylated IgG, and further comprising:
(c) quantifying the amount of IgG bound to the EndoS49 polypeptide in the first sub-sample, and the amount of IgG bound to the alternative IgG-binding reagent in the second sub-sample; and
(d) comparing both the amounts of bound IgG determined in (c);
and thereby assessing the glycosylation state or functional quality of an IgG containing sample.

The modified enzyme of the present invention may also be used in methods for isolating Fab or Fc fragments of IgG. The methods of the invention make use of a highly specific IgG cleaving enzyme from S. pyogenes, IdeS (Immunoglobulin G-degrading enzyme of S. pyogenes), and an EndoS49 polypeptide.

In one method of the invention, a sample containing IgG is contacted with IdeS and an EndoS49 polypeptide, which is a modified EndoS49 polypeptide which lacks endoglycosidase activity as described above.

In the methods of the invention, typically IdeS cleaves the IgG into Fab and Fc fragments and the EndoS49 polypeptide binds to the Fc fragments. The Fc fragments are then separated from the Fab fragments.

This method is particularly useful for isolating Fab or Fc fragments from samples comprising purified IgG. More specifically, it is useful for isolating Fab or Fc fragments from a sample comprising IgG purified using the modified EndoS49 polypeptide of the invention. However, the method can also be adapted for use on samples containing unpurified IgG, such as serum, cell lysate or cell culture medium.

Also provided are kits for carrying out the methods according to the invention.

BRIEF DESCRIPTION OF THE FIGURES

FIG. 1. ClustalW alignment of EndoS49 and EndoS reveals two different proteins. EndoS49 and EndoS was aligned using ClustalW in the software MacVector. GH18 catalytic motif (D**D*D*E) is present at position 179-186 with Glu186 as the catalytic residue.

FIG. 2. EndoS49 has activity on glycoproteins. A. 1 μg of EndoS49, its catalytic mutant and the truncated versions was incubated with 3 μg human IgG in PBS overnight at 37° C. and analyzed on a SDS-PAGE gel and with LCAlectin blot. B. 1 μg EndoS49 and EndoS49(E186L) was incubated with 3 μg of subclasses 1-4 of human IgG and analyzed as above. C. 1 μg EndoS49 and its mutants were incubated with 3 μg Alpha-1-microglobulin and analyzed on a 10% SDS-PAGE gel.

FIG. 5. Phylogenetic analysis of EndoS49 and other bacterial endoglycosidases.

FIG. 6. SDS Page gel of Avastin and Erbitux after digestion with EndoS or EndoS49 followed by IdeS digestion.

BRIEF DESCRIPTION OF THE SEQUENCES

Figure 3:
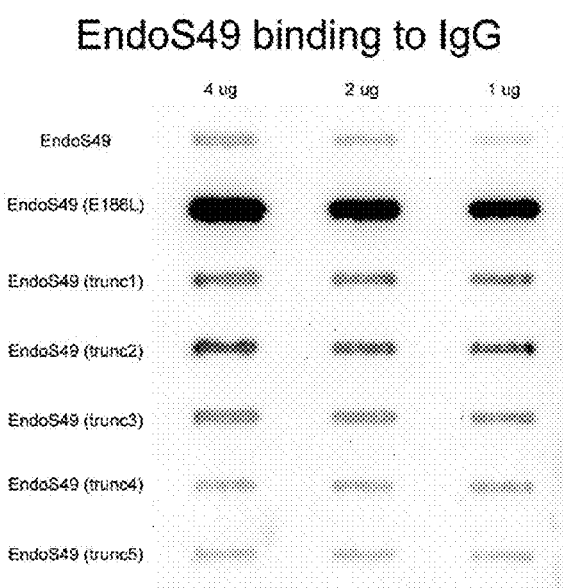
FIG. 3. EndoS49 binds to IgG. 4, 2 and 1 μg of EndoS49 and its mutants were immobilized on a PVDF membrane and incubated with human IgG and later with protein-G coupled to HRP.

SEQ ID NO: 1 is an amino acid sequence of an EndoS49 polypeptide isolated from S. pyogenes M49 serotype NZ131.

SEQ ID NO: 2 is an amino acid sequence of a modified EndoS49 polypeptide (E186L) derived from the sequence of SEQ ID NO: 1.

SEQ ID NO: 3 is a nucleotide sequence encoding EndoS49 polypeptide

SEQ ID NO: 4 is an amino acid sequence of IdeS isolated from S. pyogenes AP1.

DETAILED DESCRIPTION OF THE INVENTION

General Polypeptide Features

The present invention relates to a novel polypeptide EndoS49. The invention also provides various methods which utilize the bacterial proteins EndoS49 and IdeS, as well as other proteins. The terms protein, peptide and polypeptide are used interchangeably herein. It will be understood that certain polypeptides and methods of the invention require an EndoS49 polypeptide having endoglycosidase activity, whereas other polypeptides and methods of the invention require a modified EndoS49 polypeptide lacking said activity.

The following section relates to general features of all polypeptides of the invention, and in particular to variations, alterations, modifications or derivatisations of amino acid sequence which are included within the polypeptides of the invention. It will be understood that such variations, alterations, modifications or derivatisations of polypeptides as are described herein are subject to the requirement that the polypeptides retain any further required activity or characteristic as may be specified subsequent sections of this disclosure.

Variants of polypeptides of the invention may be defined by particular levels of amino acid identity which are described in more detail in subsequent sections of this disclosure. Amino acid identity may be calculated using any suitable algorithm. For example the PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate homology (for example used on its default settings) (Devereux et at (1984) *Nucleic Acids Research* 12, 387-395).

It will be understood that variants of polypeptides of the invention also includes substitution variants. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

The polypeptides of the invention and for use in the invention may be in a substantially isolated form. It will be understood that the polypeptide may be mixed with carriers or diluents which will not interfere with the intended purpose of the polypeptide and still be regarded as substantially isolated. A polypeptide for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

The amino acid sequence of polypeptides of the invention and for use in the invention may be modified to include non-naturally occurring amino acids or to increase the stability of the compound. When the polypeptides are produced by synthetic means, such amino acids may be introduced during production. The polypeptides may also be modified following either synthetic or recombinant production.

Polypeptides of the invention or for use in the invention may also be produced using D-amino acids. In such cases the amino acids will be linked in reverse sequence in the C to N orientation. This is conventional in the art for producing such polypeptides.

A number of side chain modifications are known in the art and may be made to the side chains of the polypeptides, subject to the polypeptides retaining any further required activity or characteristic as may be specified herein.

It will also be understood that the polypeptides of the invention and used in the invention may be chemically modified, e.g. post-translationally modified. For example, they may be glycosylated, phosphorylated or comprise modified amino acid residues. They may be modified by the addition of a signal sequence to promote insertion into the cell membrane.

The polypeptides of the invention may also be derivatised or modified to assist with their isolation or purification. Thus, in one embodiment of the invention, the polypeptide for use in the invention is derivatised or modified by addition of a ligand which is capable of binding directly and specifically to a separation means. Alternatively, the polypeptide is derivatised or modified by addition of one member of a binding pair and the separation means comprises a reagent that is derivatised or modified by addition of the other member of a binding pair. Any suitable binding pair can be used. In a preferred embodiment where the polypeptide for use in the invention is derivatised or modified by addition of one member of a binding pair, the polypeptide is preferably histidine-tagged or biotin-tagged. Typically the amino acid coding sequence of the histidine or biotin tag is included at the gene level and the proteins are expressed recombinantly in *E. coli*. The histidine or biotin tag is typically present at one end of the polypeptide, either at the N-terminus or at the C-terminus. The histidine tag typically consists of six histidine residues, although it can be longer than this, typically up to 7, 8, 9, 10 or 20 amino acids or shorter, for example 5, 4, 3, 2 or 1 amino acids. Furthermore, the histidine tag may contain one or more amino acid substitutions, preferably conservative substitutions as defined above.

EndoS49 Polypeptides Having Endoglycosidase Activity

The EndoS49 polypeptide in this instance is preferably *S. pyogenes* EndoS49, or a variant or fragment of *S. pyogenes* EndoS49 which retains endoglycosidase activity. The variant may be an EndoS49 polypeptide from another *Streptococcus equi, Streptococcus zooepidemicus* or, preferably, *Streptococcus pyogenes*

The EndoS49 polypeptide may comprise:
(a) the amino acid sequence of SEQ ID NO: 1;
(b) a variant thereof having at least 50% identity to the amino acid sequence of SEQ ID NO: 1 and having endoglycosidase activity; or (c) a fragment of either thereof having endoglycosidase activity.

Preferably, the polypeptide comprises, or consists of, the sequence of SEQ ID NO: 1. SEQ ID NO: 1 is the sequence of EndoS49 from *S. pyogenes*. The EndoS49 polypeptide of the invention may additionally not comprise a signal sequence.

Variant polypeptides as described in this section are those for which the amino acid sequence varies from that in SEQ ID NO: 1, but which retain the endoglycosidase activity of EndoS49. Such variants may include allelic variants and the deletion, modification or addition of single amino acids or groups of amino acids within the protein sequence, as long as the peptide maintains IgG endoglycosidase activity.

The variant sequences typically differ by at least 1, 2, 3, 5, 10, 20, 30, 50, 100 or more mutations (which may be substitutions, deletions or insertions of amino acids). For example, from 1 to 100, 2 to 50, 3 to 30 or 5 to 20 amino acid substitutions, deletions or insertions may be made, provided the modified polypeptide retains activity as an IgG-specific endoglycosidase.

Variants of the amino acid sequence of SEQ ID NO: 1 preferably contain residues 179 to 186 of SEQ ID NO: 1, and in particular include the motif D**D*D*E. These amino acids constitute a family 18 glycoside hydrolase catalytic domain. The glutamic acid at position 186 is essential for enzymatic activity. Most preferably, therefore, the variant of SEQ ID NO: 1 contains glutamic acid at the position equivalent to position 186 of SEQ ID NO: 1. The variant of SEQ ID NO: 1 may contain residues 179 to 186 of SEQ ID NO: 1 having one or more conservative substitutions, provided that the variant contains glutamic acid at the position equivalent to position 186 of SEQ ID NO: 1.

Typically, polypeptides which display the endoglycosidase activity of EndoS49 with more than about 50%, 55% or 65% identity, preferably at least 70%, at least 80%, at least 90% and particularly preferably at least 95%, at least 97% or at least 99% identity, with the amino acid sequence of SEQ ID NO: 1 are considered variants of the protein The identity of variants of SEQ ID NO: 1 may be measured over a region of at least 100, at least 250, at least 500, at least 750, at least 800, at least 810, at least 820, at least 930, at least 940 or more contiguous amino acids of the sequence shown in SEQ ID NO: 1, or more preferably over the full length of SEQ ID NO: 1.

The fragment of the EndoS49 polypeptide used in the invention is typically at least 400, 500, 600, 700, 750, 800, or 825 amino acids in length, as long as it retains the IgG endoglycosidase activity of EndoS. Preferably, the fragment of the EndoS49 polypeptide used in the invention encompasses residues 179 to 186 of SEQ ID NO: 1.

Polypeptides for use in the present invention may be isolated from any suitable organism that expresses an EndoS49 polypeptide or a variant of an EndoS49 polypeptide. Typically, the EndoS49 polypeptide is isolated from suitable EndoS49 expressing strains of *Streptococcus*, preferably strains of *S. pyogenes*, and in particular those of serotype M49.

Isolation and purification of EndoS49 from an expressing *S. pyogenes* culture, or from cultures of other cells expressing EndoS49 is typically on the basis of endoglycosidase activity. Preferably the purification method involves an ammonium sulphate precipitation step and an ion exchange chromatography step. According to one method, the culture medium is fractionated by adding increasing amounts of ammonium sulphate. The amounts of ammonium sulphate may be 10 to 80%. Preferably the culture medium is fractionated with 50% ammonium sulphate, and the resulting supernatant is further precipitated with 70% ammonium sulphate. Pelleted polypeptides may then be subjected to ion exchange chromatography, for example by FPLC on a Mono Q column. Eluted fractions may be assayed for endoglycosidase activity and peak activity fractions may be pooled. Fractions may be analysed by SDS PAGE. Fractions may be stored at −80° C.

Polypeptides for use in the invention may also be prepared as fragments of such isolated polypeptides. Further, the EndoS49 polypeptides may also be made synthetically or by recombinant means. For example, a recombinant EndoS49 polypeptide may be produced by transfecting mammalian cells in culture with an expression vector comprising a nucleotide sequence encoding the polypeptide operably linked to suitable control sequences, culturing the cells, extracting and purifying the EndoS49 polypeptide produced by the cells.

The EndoS49 polypeptides of invention described in this section display endoglycosidase activity. Preferably, the polypeptide hydrolyses IgG or IgG Fc fragments by hydrolysing glycan linked of a full-length IgG heavy chain polypeptide. Preferably the EndoS49 polypeptide of the invention also has endoglycosidase activity, and is capable of glycan hydrolysis of alpha-1-microglobulin.

The endoglycosidase activity may be determined by means of a suitable assay. For example, a test polypeptide may be incubated with glycoprotein such as IgG or alpha-1-microglobulin at a suitable temperature, such as 37° C. The starting materials and the reaction products may then be analysed by SDS PAGE. Typically, the molecular mass of the IgG heavy chain is reduced by approximately 3 kDa to 4 kDa if the test polypeptide has IgG endoglycosidase activity. Another assay for determining whether a test polypeptide has IgG endoglycosidase activity is by detection of glycosylated IgG using *Lens culinaris* agglutinin lectin (LCA), optionally using horseradish peroxidase and peroxidase substrate. Typically, the carbohydrate signal is reduced if the test polypeptide has IgG endoglycosidase activity. Another assay for determining whether a test polypeptide has IgG endoglycosidase activity is by incubation of a test polypeptide with purified IgG Fc fragments followed by reduction of the sample with 10 mM dithiotreitol and mass spectroscopy (MALDI-TOF) analysis. Endoglycosidase activity can also be measured for EndoS49 polypeptides by using alpha-1-microglobulin in place of IgG in the assays mentioned above.

The endoglycosidase activity of the polypeptides can be further characterised by inhibition studies.

The EndoS49 polypeptide is capable of hydrolyzing glycoprotein molecules present in a sample taken from a subject. Thus, where the subject is a human, the EndoS49 polypeptide is capable of hydrolyzing the glycans in glycoproteins of a subject, such as on the heavy chains of human IgG or alpha-1-microglobulin. EndoS49 is capable of hydrolyzing human IgG of all four subclasses ($IgG_{1-4}$). In preferred embodiments, the EndoS49 polypeptide has the ability to hydrolyze human IgG and alpha-1-microglobulin.

EndoS49 Polypeptides which Lack Endoglycosidase Activity

The EndoS49 polypeptide in this instance may also be modified *S. pyogenes* EndoS49, which has been engineered to lack endoglycosidase activity but which possesses IgG binding activity. Such modified EndoS49 is particularly useful in the methods described herein. By IgG binding activity it will be understood that the modified EndoS49 binds to IgG, or a variant or fragment thereof, in particular the Fc fragment thereof, which is normally glycosylated. By "normally glycosylated" it will be understood that the IgG molecule, or variant of fragment thereof, is a glycoprotein comprising at least the IgG polypeptide heavy chain (or variant of fragment thereof) coupled to at least one carbohydrate group as found coupled to naturally occurring IgG molecules. In particular, the at least one carbohydrate group is a glycan linked to the asparagine residue corresponding to residue 297 of a full-length IgG heavy chain polypeptide.

The EndoS49 polypeptide is preferably engineered by site-directed mutagenesis. By IgG binding activity it will be understood that the EndoS49 polypeptides described in this section bind at least one, preferably two, three or all four of the IgG subclasses, $IgG_{1-4}$. Preferably the at least one IgG subclass is bound with high affinity and/or high specificity.

By high affinity it is meant that the binding affinity constant ($K_D$) for the interaction of the modified EndoS49 with an IgG subclass is greater than 0.05 µM, preferably greater than 0.06 µM, 0.07 µM or 0.08 µM. Binding activity may be determined, and binding affinity may be assessed by any suitable means. For example, by surface plasmon resonance interaction analysis, equilibrium dialysis analysis, or any standard biochemical methods in conjunction with, for example, Scatchard analysis.

The variant may be derived from an EndoS49 polypeptide from another organism, such as another bacterium, as is described in the preceding section with the exception that the variant in this instance lacks endoglycosidase activity but possesses IgG binding activity. The modified EndoS49 polypeptide may comprise:

(a) the amino acid sequence of SEQ ID NO: 2;
(b) a variant thereof having at least 50% identity to the amino acid sequence of SEQ ID NO: 2 which lacks endoglycosidase activity; or
(c) a fragment of either thereof which lacks endoglycosidase activity.

Preferably, the polypeptide comprises, or consists of, the sequence of SEQ ID NO: 2. SEQ ID NO: 2 is derived from the sequence of SEQ ID NO: 1, but has been engineered to lack endoglycosidase activity by the substitution of glutamic acid (E) for leucine (L) at position 186 of SEQ ID NO: 1. Such polypeptides typically possess IgG-binding activity as described above.

Variant polypeptides as described in this section are those for which the amino acid sequence varies from that in SEQ ID NO: 2, but which lack endoglycosidase activity and retain IgG-binding activity. Such variants may include allelic variants and the deletion, modification or addition of single amino acids or groups of amino acids within the protein sequence, as long as the peptide maintains the above characteristics.

The variant sequences typically differ by at least 1, 2, 3, 5, 10, 20, 30, 50, 100 or more mutations (which may be substitutions, deletions or insertions of amino acids). For example, from 1 to 100, 2 to 50, 3 to 30 or 5 to 20 amino acid substitutions, deletions or insertions may be made, provided the modified polypeptide lacks endoglycosidase activity and retains IgG-binding activity.

Typically, polypeptides which lack endoglycosidase activity and retain IgG-binding activity with more than about 50%, 55% or 65% identity, preferably at least 70%, at least 80%, at least 90% and particularly preferably at least 95%, at least 97% or at least 99% identity, with the amino acid sequence of SEQ ID NO: 2 are considered variants of the protein The identity of variants of SEQ ID NO: 2 may be measured over a region of at least 100, at least 250, at least 500, at least 750, at least 800, at least 820, at least 830 or more contiguous amino acids of the sequence shown in SEQ ID NO: 2, or more preferably over the full length of SEQ ID NO: 2.

The fragment of the EndoS49 polypeptide used in the invention is typically at least 300, 400, 500, 600, 700, 750, 800 or 830 amino acids in length, as long as it lacks endoglycosidase activity and retains IgG-binding activity.

In an alternative method, an EndoS49 protein with the desired characteristics can be produced by altering a nucleotide encoding an EndoS49 protein, and then expressing said nucleotide in a suitable system. Suitable methods include site-directed mutagenesis of the nucleotide encoding the protein. This technique has been widely used in the study of protein functions. The technique is typically oligonucleotide-based and involves the following steps:

(1) Cloning the DNA encoding the protein of interest into a plasmid vector.
(2) Denaturing the plasmid DNA to produce single strands.
(3) Contacting the denatured DNA with a synthetic oligonucleotide (or oligonucleotides) complementary to the target sequence but incorporating the desired mutation(s) (point mutation, deletion, or insertion), such that the synthetic oligonucleotide anneals to the target region.
(4) Extending the mutated strand by a DNA-polymerase using the plasmid DNA strand as the template.
(5) Propagating the heteroduplex (mutated/non-mutated strand) by transformation in *E. coli*.

After propagation, about 50% of the produced heteroduplexes are mutants and the other 50% are "wild type" (no mutation). Selection and enrichment methods are used to favor the production of mutants. For example, the parental non-mutated strand can be digested with a restriction enzyme that only digests methylated DNA (DpnI). This allows removal of the parental strand from the reaction before transformation of *E. coli* by since the newly synthesized strands are un-methylated while the parental strand (if purified from the correct *E. coli* background) is methylated.

Alternatives to site-directed mutagenesis include:

(1) Polymerase chain reaction (PCR) based methods using specific mutagenic primers, or error-prone PCR with subsequent screening for desired mutations or loss/gain of protein function.
(2) Introduction of a plasmid harboring the gene of interest into an *E. coli* mutator strain (deficient in DNA proofreading systems) and subsequent screening for desired mutations or loss/gain of protein function.
(3) Chemical synthesis of partial or whole genes containing the desired mutations and subsequent introduction into an appropriate protein expression system.

Alternatively, an EndoS49 protein with the desired characteristics can be produced by DNA-independent methods, which include chemical synthesis of parts of a polypeptide with the desired mutation.

Polypeptides for use in the invention may also be prepared as fragments of such isolated polypeptides. Further, the EndoS49 polypeptides may also be made synthetically or by recombinant means. For example, a recombinant EndoS49 polypeptide may be produced by transfecting mammalian cells in culture with an expression vector comprising a nucleotide sequence encoding the polypeptide operably linked to suitable control sequences, culturing the cells, extracting and purifying the EndoS49 polypeptide produced by the cells.

The EndoS49 polypeptide is capable of binding to IgG molecules present in a sample taken from a subject. Thus, where the subject is a human, the EndoS49 polypeptide is capable of binding human IgG. EndoS49 is capable of binding human IgG of all four subclasses (IgG$_{1-4}$).

Polynucelotides, Vectors and Host Cells

The invention also relates to polynucleotides encoding the above polypeptides, and their use in medicine. In particular the invention relates to polynucleotides comprising or consisting of (a) the coding sequence of SEQ ID NO:3 or a complementary sequence thereto; (b) sequence which hybridises under stringent conditions to the sequences defined in (a); (c) sequence which is degenerate as a result of the genetic code to sequence as defined in (a) or (b); (d) sequence having at least 60% identity to sequences defined in (a) (b) or (c); and (e) fragments of the above sequences.

Typically the polynucleotide is DNA. However, the invention may comprise RNA polynucleotides. The polynucleotides may be single or double stranded, and may include within them synthetic or modified nucleotides.

A polynucleotide of the invention can hybridize to the coding sequence or the complement of the coding sequence of SEQ ID NO: 3 at a level significantly above background. Background hybridization may occur, for example, because of other DNAs present in a DNA library. The signal level generated by the interaction between a polynucleotide of the invention and the coding sequence or complement of the coding sequence of SEQ ID NO: 3 is typically at least 10 fold, preferably at least 100 fold, as intense as interactions between other polynucleotides and the coding sequence of SEQ ID NO: 3. The intensity of interaction may be measured, for example, by radiolabelling the probe, e.g. with $^{32}$P. Selective hybridisation may typically be achieved using conditions of medium to high stringency. However, such hybridisation may be carried out under any suitable conditions known in the art (see Sambrook et al, 1989. For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 3 may be modified by nucleotide substitutions, for example from 1, 2 or 3 to 10, 25, 50 or 100 substitutions. The polynucleotide of SEQ ID NO: 3 may alternatively or additionally be modified by one or more insertions and/or deletions and/or by an extension at either or both ends. Additional sequences such as signal sequences may also be included. The modified polynucleotide generally encodes a polypeptide which has endoglycosidase activity. Alternatively, a polynucleotide encodes an epitope portion of an EndoS49 polypeptide. Degenerate substitutions may be made and/or substitutions may be made which would result in a conservative amino acid substitution when the modified sequence is translated, for example as shown in the Table above.

A nucleotide sequence which is capable of selectively hybridizing to the complement of the DNA coding sequence of SEQ ID NO: 3 will generally have at least 60%, at least 70%, at least 80%, at least 90%, at least 95%, at least 98% or at least 99% sequence identity to the coding sequence of SEQ ID NO: 3 over a region of at least 20, preferably at least 30, for instance at least 40, at least 60, more preferably at least 100 contiguous nucleotides or most preferably over the full length of SEQ ID NO: 3. Methods for the calculation of sequence identity or similarity are discussed in more detail above in relation to the polypeptides of the invention.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 25, preferably over 30 nucleotides forms one aspect of the invention, as does a polynucleotide which has at least 95% sequence identity over 40 nucleotides.

Polynucleotide fragments, such as those suitable for use as probes or primers will preferably be at least 10, preferably at least 15 or at least 20, for example at least 25, at least 30 or at least 40 nucleotides in length. They will typically be up to 40, 50, 60, 70, 100 or 150 nucleotides in length. Probes and fragments can be longer than 150 nucleotides in length, for example up to 200, 300, 400, 500, 600, 700 nucleotides in length, or even up to a few nucleotides, such as five or ten nucleotides, short of the coding sequence of SEQ ID NO: 3.

Polynucleotides according to the invention may be produced recombinantly, synthetically, or by any means available to those of skill in the art. They may also be cloned by standard techniques. The polynucleotides are typically provided in isolated and/or purified form.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the ndoS49 gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Although in general the techniques mentioned herein are well known in the art, reference may be made in particular to Sambrook et al, Molecular Cloning: A Laboratory Manual, 1989.

The polynucleotides according to the invention have utility in production of the polypeptides according to the invention, which may take place in vitro. Polynucleotides of the invention may be used as a primer, e.g. a PCR primer, a primer for an alternative amplification reaction, a probe e.g. labelled with a revealing label by conventional means using radioactive or non-radioactive labels, or the polynucleotides may be cloned into vectors.

Polynucleotides or primers of the invention may carry a revealing label. Suitable labels include radioisotopes such as $^{32}$P or $^{35}$S, enzyme labels, or other protein labels such as biotin. Such labels may be added to polynucleotides or primers of the invention and may be detected using techniques known per se.

Polynucleotides or primers of the invention or fragments thereof, labelled or unlabelled, may be used by a person skilled in the art in nucleic acid-based tests for detecting or sequencing ndoS49 in a sample.

Such tests for detecting generally comprise bringing a sample containing DNA or RNA into contact with a probe comprising a polynucleotide or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which has hybridized to the probe. Alternatively, the sample nucleic acid may be immobilized on a solid support, and the amount of probe bound to such a support can be detected.

The probes of the invention may conveniently be packaged in the form of a test kit in a suitable container. In such kits the probe may be bound to a solid support where the assay formats for which the kit is designed requires such binding. The kit may also contain suitable reagents for treating the sample to be probed, hybridizing the probe to nucleic acid in the sample, control reagents, instructions, and the like.

The polynucleotides of the invention may be incorporated into a recombinant replicable vector. The vector may be used to replicate the nucleic acid in a compatible host cell. Therefore, polynucleotides of the invention may be made by introducing a polynucleotide of the invention into a replicable vector, introducing the vector into a compatible host cell and growing the host cell under conditions which bring about replication of the vector.

Preferably the vector is an expression vector comprising a nucleic acid sequence that encodes a polypeptide of the invention. Such expression vectors are routinely constructed in the art of molecular biology and may for example involve the use of plasmid DNA and appropriate initiators, promoters, enhancers and other elements, which may be necessary, and which are positioned in the correct orientation, in order to allow for protein expression. Other suitable vectors would be apparent to persons skilled in the art. By way of further example in this regard we refer to Sambrook et al. 1989.

Polynucleotides according to the invention may also be inserted into the vectors described above in an antisense orientation in order to provide for the production of antisense RNA. Antisense RNA or other antisense polynucleotides or interfering RNA, iRNA may also be produced by synthetic means. Such antisense polynucleotides or iRNA may be used as test compounds in the assays of the invention or may be useful in a method of treatment of the human or animal body by therapy.

Preferably, a polynucleotide of the invention or for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with a origin of replication, optionally a promoter for the expression of the said polynucleotide and optionally a regulator of the promoter. The vectors may contain one or more selectable marker genes, for example an ampicillin resistence gene in the case of a bacterial plasmid or a resistance gene for a fungal vector.

Promoters and other expression regulation signals may be selected to be compatible with the host cell for which expression is designed. For example, yeast promoters include S. cerevisiae GAL4 and ADH promoters, S. pombe nmt1 and adh promoter. Mammalian promoters include the metallothionein promoter which can be induced in response to heavy metals such as cadmium. Viral promoters such as the SV40 large T antigen promoter or adenovirus promoters may also be used. All these promoters are readily available in the art.

Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

Expression vectors may be transformed into a suitable host cell to provide for expression of a polypeptide or polypeptide fragment of the invention. The host cell, transformed or transfected with an expression vector as described above, is cultivated under conditions to allow for expression of the polypeptide or fragment, and the expressed polypeptide or fragment is recovered. Isolation and purification may be carried out as described above. Host cells will be chosen to be compatible with the vector and will preferably be bacterial. Host cells may also be cells of a non-human animal, or a plant transformed with a polynucleotide of the invention.

IdeS

IdeS is an extracellular cysteine protease produced by the human pathogen *S. pyogenes* and is described in WO 03/051914. IdeS was originally isolated from a group A streptococcal strain of serotype M1, but the ides gene has now been identified in all tested group A streptococcal strains. IdeS has an extraordinarily high degree of substrate specificity, with its only identified substrate being IgG. IdeS catalyses a single proteolytic cleavage in the lower hinge region of human IgG. This proteolytic degradation promotes inhibition of opsonophagocytosis and interferes with the killing of group A *Streptococcus*. IdeS also cleaves some subclasses of IgG in various animals and efficiently converts IgG into Fc and Fab fragments. The ides gene has been cloned and expressed in *E. coli* as a GST fusion protein.

The IdeS polypeptide for use in the methods of the invention is preferably *S. pyogenes* IdeS, or a variant or fragment of *S. pyogenes* IdeS which retains cysteine protease activity. The variant may be an IdeS polypeptide from another organism, such as another bacterium. The bacterium is preferably a *Streptococcus*. The *Streptococcus* is preferably a group A *Streptococcus*, a group C *Streptococcus* or a group G *Streptococcus*. In particular, the variant may be an IdeS polypeptide from a group C *Streptococcus* such as *S. equii* or *S. zooepidemicus*. Alternatively, the variant may be from *Pseudomonas putida*.

The IdeS polypeptide may comprise:
(a) the amino acid sequence of SEQ ID NO: 4;
(b) a variant thereof having at least 50% identity to the amino acid sequence of SEQ ID NO: 4 and having IgG cysteine protease activity; or
(c) a fragment of either thereof having IgG cysteine protease activity.

Preferably, the IdeS polypeptide comprises, or consists of, the sequence of SEQ ID NO: 4. SEQ ID NO: 4 is the sequence of the mature form of IdeS, without the signal sequence.

Variant IdeS polypeptides are those for which the amino acid sequence varies from that in SEQ ID NO: 4, but which display the same IgG cysteine protease activity as IdeS. Typically, polypeptides with more than about 50%, 55% or 65% identity, preferably at least 70%, at least 80%, at least 90% and particularly preferably at least 95%, at least 97% or at least 99% identity, with the amino acid sequence of SEQ ID NO: 4 are considered variants of the protein. Such variants may include allelic variants and the deletion, modification or addition of single amino acids or groups of amino acids within the protein sequence, as long as the peptide maintains the basic functionality of IdeS. The identity of variants of SEQ ID NO: 4 may be measured over a region of at least 50, at least 75, at least 100, at least 150, at least 200, at least 250, at least 275, at least 300 or more contiguous amino acids of the sequence shown in SEQ ID NO: 4, or more preferably over the full length of SEQ ID NO: 4.

Variants of the amino acid sequence of SEQ ID NO: 4 preferably contain residues Lys-55 and/or Cys-65 and/or His-233 and/or Asp-255 and/or Asp-257 of SEQ ID NO: 4. Most preferably, the variant of SEQ ID NO: 4 contains each of residues Lys-55, Cys-65, His-233, Asp-255 and Asp-257 of SEQ ID NO: 4.

The variant sequences typically differ by at least 1, 2, 5, 10, 20, 30, 50 or more mutations (which may be substitutions, deletions or insertions of amino acids). For example, from 1 to 50, 2 to 30, 3 to 20 or 5 to 10 amino acid substitutions, deletions or insertions may be made. The modified polypeptide retains activity as an IgG-specific cysteine protease. Preferably the variant polypeptides comprise a cysteine residue and a histidine residue at a spacing typically found in cysteine proteases. For example, in SEQ ID NO: 4, these residues are found at a spacing of about 130 amino acids, as is typically found in cysteine proteases.

The fragment of the IdeS polypeptide used in the invention is typically at least 10, for example at least 15, 20, 25, 30, 40, 50 or more amino acids in length, up to 100, 150, 200, 250 or 300 amino acids in length, as long as it retains the IgG cysteine protease activity of IdeS. Preferably, the fragment of the IdeS polypeptide used in the invention encompasses residues Lys-55 and/or Cys-65 and/or His-233 and/or Asp-255 and/or Asp-257 of SEQ ID NO: 4. Most preferably, the fragment encompasses each of residues Lys-55, Cys-65, His-233, Asp-255 and Asp-257 of SEQ ID NO: 4.

IdeS polypeptides for use in accordance with the invention display immunoglobulin cysteine protease activity, and in particular IgG cysteine protease activity. Preferably, the polypeptide cleaves IgG in the hinge region and more particularly in the hinge region of the heavy chain. Cleavage results in production of Fc and Fab fragments of IgG. Preferably the activity is specific for IgG. The cysteine protease activity may be determined by means of a suitable assay. For example, a test polypeptide may be incubated with IgG at a suitable temperature, such as 37° C. The starting materials and the reaction products may then be analysed by SDS PAGE to determine whether the desired IgG cleavage product is present. Typically this cleavage product is a 31 kDa fragment. Typically there is no further degradation of IgG after this first cleavage. The cleavage product may be subjected to N-terminal sequencing to verify that cleavage has occurred in the hinge region of IgG. Preferably the N-terminal sequence comprises the sequence GPSVFLFP.

The cysteine protease activity of the polypeptides can be further characterised by inhibition studies. Preferably, the activity is inhibited by the peptide derivate Z-LVG-CHN$_2$ and/or by iodoacetic acid both of which are protease inhibitors. However, the activity is generally not inhibited by E64.

The cysteine protease activity of the polypeptides is generally IgG-specific in that the polypeptides may not degrade the other classes of Ig, namely IgM, IgA, IgD and IgE, when incubated with these immunoglobulins under conditions that permit cleavage of IgG. The IdeS polypeptide is capable of cleaving human IgG. In preferred embodiments the polypeptide has the ability to cleave human, rabbit, mouse or goat IgG.

IdeS polypeptides for use in the present invention may be isolated from any suitable organism that expresses an IdeS polypeptide. Typically, the IdeS polypeptide is isolated from suitable IdeS expressing strains of S. pyogenes. Suitable organisms and strains may be identified by a number of techniques. For example, S. pyogenes strains may initially be tested for the presence an ides gene. The presence of the ides gene can then be verified by PCR using the primers or by hybridisation of the probes to genomic DNA of the S. pyogenes strain.

S. pyogenes strains expressing active IdeS can be identified by assaying for IgG cysteine protease activity in the culture supernatant. Preferably inhibitor E64 is added to the supernatant to inhibit any SpeB cysteine protease activity. At least five strains express active IdeS: strains AP1, AP12, AP55, KTL3 and SF370. Preferably the expressing strain is selected from AP1, AP12 and AP55.

Isolation and purification of IdeS from an expressing S. pyogenes culture, or from cultures of other cells expressing IdeS is typically on the basis of IgG cysteine protease activity. Preferably the purification method involves an ammonium sulphate precipitation step and an ion exchange chromatography step. According to one method, the culture medium is fractionated by adding increasing amounts of ammonium sulphate. The amounts of ammonium sulphate may be 10 to 80%. Preferably the culture medium is fractionated with 50% ammonium sulphate, and the resulting supernatant is further precipitated with 70% ammonium sulphate. Pelleted polypeptides may then be subjected to ion exchange chromatography, for example by FPLC on a Mono Q column. Eluted fractions may be assayed for IgG cysteine protease activity and peak activity fractions may be pooled. Fractions may be analysed by SDS PAGE. For example, an N-terminal sequence can be obtained from the SDS PAGE protein band. Fractions may be stored at −20° C.

Methods Using the Endoglycosidase Activity of EndoS49

As described herein, EndoS49 has endoglycosidase activity and is able to hydroylse the glycan of glycoproteins including IgG and alpha-1-microglobulin. The present invention thus provides methods for deglycosylation of glycoproteins, and in particular, hydrolysis of glycan from glycoproteins, and in particular, from IgG and alpha-1-microglobulin. Typically, such a method includes incubating a sample containing glycoprotein with EndoS49 with a glycoprotein under conditions which allow the endoglycosidase activity. Suitable conditions include use of EndoS49 at a concentration of at least 1 μg/ml, 2 μg/ml, 4 μg/ml, 6 μg/ml, 8 μg/ml, 10 μg/ml, 12 μg/ml, 15 μg/ml or 20 μg/ml, preferably at least 10 μg/ml. Suitable conditions also include incubation of the sample with EndoS49 for at least 20 minutes, 30 minutes, 40 minutes, 50 minutes, 60 minutes, 70 minutes, 80 minutes, 90 minutes or 120 minutes, preferably at least 60 minutes. Incubation preferably takes place at room temperature, more preferably at approximately 20° C., 25° C., 30° C., 35° C., 40° C. or 45° C., and most preferably at approximately 37° C.

These methods may be used to provide deglycosylated glycoproteins, which may themselves be useful in research or therapy. These methods may also be used to characterise glycans on glycoproteins, for example, in glycomapping or glycoprofiling. Such glycomapping and glycoprofiling is particularly useful for antibody molecules, such as IgG molecules, for example, in the analysis of monoclonal IgG molecules. Typically, the methods involved incubating the protein with EndoS49 to hydroylase the glycans of the protein. Subsequently, the glycans and the protein or polypeptide are separated, for example, using any suitable technique such as HPLC or gel chromatography. The separated moieties can then be analysed using any suitable analytical method, such as mass spectrometry, HPLC, gel chromatography, gel electrophoresis, spectrometry, capillary electrophoresis and other standard laboratory techniques for the analysis of glycans and/or proteins.

In accordance with additional methods of the present invention, the methods may also comprise utilising additional enzymes such as IdeS so that the glycans on the Fc portion of the antibody can be analysed in more details using the methods and techniques described herein.

One example is to analyze the fucosylation of an immunoglobulin. The degree of fucosylation on the Fc glycans on an IgG molecule is important for the therapeutic potential of an IgG drug candidate. Afucosylated IgG molecules increase the ADCC (nn) effect of the therapeutic IgG molecule. Thus, in accordance with the present invention, there is provided a method for analyzing the amount of fucose in the Fc glycans of an IgG, using EndoS49.

Typically, such a method includes incubating an glycoprotein, in this case an immunoglobulin, with EndoS49 under conditions which allow the endoglycosidase activity of EndoS49. Suitable conditions include use of EndoS49 at a concentration of at least 1 µg/ml, 2 µg/ml, 4 µg/ml, 6 µg/ml, 8 µg/ml, 10 µg/ml, 12 µg/ml, 15 µg/ml or 20 µg/ml, preferably at least 10 µg/ml. Suitable conditions also include incubation of the sample with EndoS49 for at least 20 minutes, 30 minutes, 40 minutes, 50 minutes, 60 minutes, 70 minutes, 80 minutes, 90 minutes or 120 minutes, preferably at least 60 minutes. Incubation preferably takes place at room temperature, more preferably at approximately 20° C., 25° C., 30° C., 35° C., 40° C. or 45° C., and most preferably at approximately 37° C. IdeS may be added after the reaction with EndoS49, or in the same reaction mixture, to induce proteolysis, dividing the immunoglobulin molecule into F(ab')2 and Fc. The two fragments are separated using a separation method before injection into a mass spectrometer. After glycan cleavage, a GlcNAc and core Fuc residue remain attached to Asn at the consensus Fc/2 glycosylation site. Since an afocusylated immunoglobulin is not core fucosylated, some Fc/2 will contain only a GlcNAc after digestion. The characteristic mass difference (−146 Da) resulting from the absence of fucose is readily apparent in the deconvoluted mass spectrum. Use of EndoS49 therefore, facilitates the direct estimation of the degree of core afucosylation of IgG.

Method for Determining the Presence or Absence of IgG in a Sample, or for Isolating IgG from an IgG-containing Sample The isolation and/or detection of IgG is typically carried out in the art using such agents as Protein G or Protein A. These bacterial proteins interact well with IgG. However, Protein A does not bind to all four IgG subclasses (IgG$_{1-4}$), and both Protein A and Protein G are unable to discriminate between unglycosylated and/or denatured, inactive IgG and glycosylated and/or native, functionally active IgG. By contrast, the present inventors have identified that EndoS49 polypeptides which lack IgG endoglycosidase activity typically bind all four IgG subclasses with high affinity, and are selective for normally glycosylated IgG, i.e. IgG in its native, functionally active form.

Accordingly, the present invention provides an improved method for determining the presence or absence of IgG in a sample, which method comprises contacting said sample with an EndoS49 polypeptide which lacks IgG endoglycosidase activity, separating said EndoS49 from the contacted sample, and thereby determining the presence or absence of IgG and, optionally, where IgG is present, obtaining isolated IgG. The invention therefore also provides a method for isolating IgG from an IgG-containing sample, which method comprises contacting said sample with an EndoS49 polypeptide which lacks IgG endoglycosidase activity, separating said EndoS49 from the contacted sample, and thereby obtaining isolated IgG.

The above samples are contacted with EndoS49 polypeptide under conditions suitable for interaction between the polypeptide and the sample to take place and IgG binding activity to occur, i.e. to allow formation of a IgG-EndoS49 polypeptide complex. Suitable conditions include use of EndoS49 at a concentration of at least 1 µg/ml, 2 µg/ml, 4 µg/ml, 6 µg/ml, 8 µg/ml, 10 µg/ml, 12 µg/ml, 15 µg/ml or 20 µg/ml, preferably at least 10 µg/ml. Suitable conditions also include incubation of the sample with EndoS49 for at least 20 minutes, 30 minutes, 40 minutes, 50 minutes, 60 minutes, 70 minutes, 80 minutes, 90 minutes or 120 minutes, preferably at least 60 minutes. Incubation preferably takes place at room temperature, more preferably at approximately 20° C., 25° C., 30° C., 35° C., 40° C. or 45° C., and most preferably at approximately 37° C.

A particular advantage of EndoS49 in these methods is that EndoS49 specifically binds to normally glycosylated IgG. The IgG binding activities of other IgG binding agents typically require or are enhanced by denaturation of the IgG glycoprotein. This is typically achieved by treating an IgG-containing sample with acid. Such treatment may damage or denature some antibodies (acid-sensitive antibodies). Since the method of the invention requires no such treatment, the method is particularly suitable for isolating acid-sensitive IgG in its native form from a sample.

The EndoS49 may be separated from the contacted sample by any suitable method. A preferred method for removal of the EndoS49 from a sample comprises using an EndoS49 which is derivatised or modified as described above.

A preferred modification comprises the addition of a histidine tag. The presence of a histidine tag means that the polypeptide binds with a high affinity to a reagent or separating means containing chelating groups on its surface which carry a nickel, copper or zinc ion. The histidine tag binds strongly to these metal ions. Such a reagent can therefore be used to separate EndoS49 from a sample.

Another preferred modification comprises the addition of a biotin tag. The presence of a biotin tag means that the polypeptide binds with a high affinity to a reagent or separating means comprising streptavidin. The biotin tag binds strongly to streptavidin. Such a reagent can therefore be used to separate EndoS49 from a sample.

Preferred reagents or separating means are populations of magnetic particles capable of binding to the EndoS49 polypeptide. For example, where the EndoS49 polypeptide is derivatised with a histidine tag, the magnetic particles contain on their surface chelating groups which carry a nickel, copper or zinc ion. Alternatively, where the EndoS49 polypeptide is derivatised with a biotin tag, the magnetic particles contain on their surface streptavidin.

Accordingly, a preferred method of removing EndoS49 from a sample comprises using a population of magnetic particles as described above and carrying out magnetic field separation on the sample. The magnetic particles are preferably magnetic nanoparticles, and the magnetic field separation is preferably high-gradient magnetic field separation.

It will be understood that any suitable separation means may be used. For example, the alternative means described in the preceding section.

The EndoS49 of the contacted sample may be assessed for the presence or absence of bound IgG by any suitable means.

For example, the molecular weight of the EndoS49 may be analysed. EndoS49 bound to IgG will have a higher molecular weight than EndoS49 not bound to IgG. Accordingly suitable methods include any method able to discriminate protein species by weight, for example SDS-PAGE and Western Blot, Mass spectrometry etc. Alternatively, the above Western Blot may be directly analysed for the presence of IgG by using IgG-specific antibodies or antibodies specific to a particular IgG sub-class. Detection of proteins in a blot in this manner is a widely used technique in the art.

Other suitable means for detecting the presence or absence of IgG bound to EndoS49 include incubating the EndoS49 with antibodies to IgG or IgG-binding proteins with coupled enzymes (e.g. horseradish peroxidase, alkaline phosphatase) followed by addition of fluorogenic/chromogenic substrates. In this instance, the development of a colour signal indicates the presence of IgG, with the quantity of IgG being proportional to the strength of the signal. Detection of proteins in this manner is a widely used technique in the art.

Further suitable means for detecting the presence or absence of IgG bound to EndoS49 comprise first separating bound IgG from EndoS49 so that it can be analysed/detected independently of EndoS49 by any of the above methods or any suitable method. IgG may be separated from EndoS49 by any suitable means. Suitable means include the elution of IgG from EndoS49 by contacting the EndoS49 from the contacted sample with a suitable elution buffer. The choice of elution buffer will typically depend on whether or not the IgG bound to EndoS49 is known or suspected to be acid-sensitive, i.e. denatured/inactivated by contact with acids.

Where the antibody is not acid-sensitive, an elution protocol using a low pH elution buffer may typically be employed. Elution protocols of this type are well known in the art. Such elution buffers have a pH typically below about pH 3, most preferably below about pH 2. Preferred examples include 0.1 M Glycine at pH2. In addition, or optionally, such elution buffers may typically comprise at least one of the following:

Sodium or potassium salts, preferably at a concentration of about 0.5M to about 1M;
Mono-, di-, or polysaccharides with structures similar to the glycan associated with Asn-297 on native IgG;
or any combination thereof However, as outlined above, the methods of the invention are particularly suitable for detection/isolation of acid-sensitive antibodies. Where the IgG bound to EndoS49 is known or suspected to be acid-sensitive, it is therefore preferable to use elution buffers and protocols which do not require a low pH. Such protocols are also known in the art and are based on the principle of providing a buffer comprising a molecule which competes with the bound IgG for binding to EndoS49, thus leading to release of the bound IgG. Suitable competition elution buffers therefore typically comprise one or more mono-, di-, or polysaccharides with structures similar to the glycan associated with Asn-297 on native IgG. Particularly preferred elution buffers comprise sucrose at about 0.25M to about 0.5M, preferably with pH from about 5.3 to about 8.3. Examples of specific preferred elution buffers include, for example: Sucrose 0.25M, in PBS pH7.4; Sucrose 0.5M, in PBS pH7.4; Sucrose 0.25M, in PBS pH5.3; Sucrose 0.25M, in PBS pH8.5 and Sucrose 0.25M, Maltose 0.25M, in PBS pH7.4.

In addition, or optionally, such competition elution buffers may typically comprise Sodium or potassium salts, preferably at a concentration of about 0.5M to about 1M.

The means for separating bound IgG from EndoS49 as described above may also be used to obtain isolated IgG.

Method of Assessing the Glycosylation State and/or Functional Quality of an IgG Containing Sample The EndoS49 polypeptides of the invention in unmodified form have the ability to hydrolyse glycan of IgG. Also, as described above, the EndoS49 polypeptides of the invention lacking IgG endoglycosidase activity and having IgG binding activity are specific for glycosylated and/or native, functionally active IgG. Thus, the EndoS49 polypeptides can be used for analysing the glycosylation state of a glycoprotein, and in particular an IgG antibody.

In accordance with one aspect of the invention, an IgG antibody is incubated with an EndoS49 polypeptide of the invention which has endoglycosidase activity. The products obtained can be analysed by any suitable techniques, including HPLC, mass spec, gel chromatography, gel electrophoresis, spectrophotometer, capillary electrophoresis. Such methods of analysis can be conducted at any stage in the preparation of a protein, for example during screening of drug candidates, during development of production processes of biologic drugs as well as a quality control in release assays and during production.

The EndoS49 polypeptides which have been modified to remove or reduce the endoglycosidase activity, or which retain the ability to bind to IgG in its native form can also be useful in glycomapping, and in particular the analysis of glycoprotein, and in particular IgG structure.

For example, by using said EndoS49 polypeptides, optionally in combination with an alternative IgG-binding reagent, the present invention provides a method of assessing the glycosylation state or functional quality of an IgG containing sample, which method comprises taking a first and a second sub-sample from the IgG-containing sample, contacting the first sub-sample with an EndoS49 polypeptide as described in the preceding section and the second sub-sample with an alternative IgG-binding reagent which is capable of binding unglycosylated and/or denatured, inactive IgG, and then quantifying the amount of IgG bound to the EndoS49 polypeptide in the first sub-sample, and the amount of IgG bound to the alternative IgG-binding reagent in the second sub-sample. Finally, by comparing both of the amounts of bound IgG determined in the first and second sub-samples, the glycosylation state or functional quality of an IgG containing sample can be assessed.

The alternative IgG-binding reagent is typically Protein A or Protein G, which bind to all forms (native or denatured) of IgG. In this instance, the amount of IgG bound to said reagent therefore represents the total IgG present in the second sub-sample. The EndoS49 polypeptide binds only to glycosylated and/or native, functionally active IgG, and therefore the amount of IgG bound to EndoS49 represents only the glycosylated and/or native, functionally active IgG present in the first sub-sample. By comparing the concentration of total IgG from the second sub-sample to the concentration of native IgG in the first sample, the skilled person will recognise that one obtains a ratio which reflects the proportion of IgG in the original sample which is present in its glycosylated and/or native, functionally active form.

In another embodiment, the alternative IgG-binding reagent could be specific for unglycosylated and/or denatured IgG. Such a reagent could be, for example, an antibody. Accordingly, in this embodiment the proportion of IgG in the original sample which is present in its glycosylated and/or native, functionally active form can be assessed by the formula:

Amount of IgG in first sub-sample/(amount of IgG in first sub-sample+amount of IgG in second sub-sample)

The samples in the above methods are contacted with EndoS49 polypeptide or alternative IgG-binding reagent under conditions suitable for interaction between the polypeptide or reagent and the sample to take place and IgG binding activity to occur. Suitable conditions are, for example, equivalent to those set out in the preceding section.

Method for Isolating IgG Fab or Fc Fragments from an IgG-containing Sample

The methods of the present invention can be used for isolating Fab fragments from IgG-containing samples. In one embodiment, the present invention provides a method for isolating Fab fragments of IgG from an IgG-containing sample, which method comprises:
  (a) contacting said IgG-containing sample with IdeS, and an EndoS49 polypeptide;
  (b) separating said IdeS and said EndoS49 polypeptide from the contacted sample; and
thereby isolating Fab fragments.

Preferred methods for separating IdeS and EndoS49 polypeptide from a sample comprises using an IdeS and/or EndoS49 polypeptide which is derivatised or modified as described above. The same or a different modification may be used on each of IdeS and the EndoS49 polypeptide.

A preferred modification comprises the addition of a histidine tag. The presence of a histidine tag means that the polypeptide binds with a high affinity to a reagent or separating means containing chelating groups on its surface which carry a nickel, copper or zinc ion. The histidine tag binds strongly to these metal ions. Such a reagent can therefore be used to separate IdeS and/or EndoS49 polypeptide from a sample.

Another preferred modification comprises the addition of a biotin tag. The presence of a biotin tag means that the polypeptide binds with a high affinity to a reagent or separating means comprising streptavidin. The biotin tag binds strongly to streptavidin. Such a reagent can therefore be used to separate IdeS and/or EndoS49 polypeptide from a sample.

Preferred reagents or separating means are populations of magnetic particles capable of binding to the EndoS49 polypeptide. For example, where the IdeS and/or EndoS49 polypeptide is derivatised with a histidine tag, the magnetic particles contain on their surface chelating groups which carry a nickel, copper or zinc ion. Alternatively, where the IdeS and/or EndoS49 polypeptide is derivatised with a biotin tag, the magnetic particles contain on their surface streptavidin.

Accordingly, a preferred method of removing EndoS49 from a sample comprises using a population of magnetic particles as described above and carrying out magnetic field separation on the sample. The magnetic particles are preferably magnetic nanoparticles, and the magnetic field separation is preferably high-gradient magnetic field separation.

Thus, step (a) of the above method preferably additionally comprises contacting the sample with a population of magnetic nanoparticles capable of binding to IdeS and the EndoS49 polypeptide, and wherein step (b) comprises carrying out magnetic field separation on the sample.

The EndoS49 polypeptide is preferably a modified EndoS49 polypeptide lacking endoglycosidase activity.

In the above embodiment of the invention, the IgG-containing sample typically comprises purified or isolated IgG. By "purified or isolated IgG" is meant an IgG fraction with a purity of normal commercial grade. IgG is typically isolated from a sample such as serum or, in the case of recombinant IgG, from cell lysate. Isolation may be carried out according to any suitable method, preferably according to the method described above for the isolation of IgG using a modified EndoS49 polypeptide lacking endoglycosidase activity. Thus, one embodiment of the invention encompasses the method set out above comprising, prior to step (a):
  (i) contacting said IgG-containing sample with an EndoS49 polypeptide which lacks IgG endoglycosidase activity, to thereby allow formation of a IgG-EndoS49 polypeptide complex;
  (ii) separating said IgG-EndoS49 polypeptide complex from the contacted sample;
  (iii) eluting IgG from the IgG-EndoS49 polypeptide complex thereby obtaining an IgG-containing sample;
and wherein steps (a) and (b) are carried out the IgG-containing sample obtained in step (iii). Separation of the IgG-EndoS49 polypeptide complex from a sample is preferably carried out according to the methods set out in the section above relating to methods for determining the presence or absence of IgG in a sample, or for isolating IgG from an IgG-containing sample.

In an alternative embodiment of the invention, the methods are adapted to isolate Fab fragments from IgG-contained samples without the need to purify the IgG before carrying out the method. These methods can be carried out on a sample containing unpurified IgG, for example, whole serum, cell lysate or cell culture medium. In this embodiment of the invention, the method comprises:
  (a) contacting said IgG-containing sample with an EndoS49 polypeptide to thereby allow formation of a IgG-EndoS49 polypeptide complex;
  (b) separating said IgG-EndoS49 polypeptide complex from the contacted sample;
  (c) adding to IgG-EndoS49 polypeptide complexes obtained in step (b) IdeS; and (d) separating said IdeS and said EndoS49 polypeptide from the mixture obtained in (c);
  and thereby isolating Fab fragments.

The methods for separating IdeS and/or EndoS49 polypeptide from the samples/mixtures above preferably comprise using an IdeS and/or EndoS49 polypeptide which is derivatised or modified as described above. The same or a different modification may be used on each of IdeS and the EndoS49 polypeptide. Preferred reagents or separating means are populations of magnetic particles capable of binding to the IdeS and/or EndoS49 polypeptide. For example, where the IdeS and/or EndoS49 polypeptide is derivatised with a histidine tag, the magnetic particles contain on their surface chelating groups which carry a nickel, copper or zinc ion. Alternatively, where the IdeS and/or EndoS49 polypeptide polypeptide is derivatised with a biotin tag, the magnetic particles contain on their surface streptavidin.

Thus, step (a) of the above method preferably additionally comprises contacting the sample with a population of magnetic nanoparticles capable of binding to the EndoS49 polypeptide, step (c) additionally comprises contacting the IgG-EndoS49 polypeptide complexes obtained in step (b) with a population of magnetic nanoparticles capable of binding to IdeS and the EndoS49 polypeptide, and wherein steps (b) and (d) comprise carrying out magnetic field separation on the sample of (a) and mixture obtained in (c), respectively.

It will be understood that any suitable separation means may be used. For example, the alternative means described in the section relating to methods for isolating a population of cells which are substantially free of IgG molecules bound to FcγRs could be adapted for separation of IdeS and/or EndoS49 polypeptide.

The EndoS49 polypeptide in the above embodiment is preferably a modified EndoS49 polypeptide lacking endoglycosidase activity.

The above methods of the invention can also be used for isolating Fc fragments from IgG-containing samples. In one such embodiment of the invention, the method comprises:
(a) contacting said IgG-containing sample with IdeS;
(b) separating IdeS from the mixture obtained in step (a), thereby isolating Fab and Fc fragments;
(c) contacting said Fab and Fc fragments with an EndoS49 polypeptide to thereby allow formation of a Fc fragment-EndoS49 polypeptide complex;
(d) separating the Fc fragment-EndoS49 polypeptide complexes from the mixture obtained in step (c); and
(e) isolating Fc fragments from the Fc fragment-EndoS49 polypeptide complexes obtained in step (d).

It will be understood that any suitable separation means may be used as described above, however, the methods for separating IdeS and/or EndoS49 polypeptide from the samples/mixtures above preferably comprise using an IdeS and/or EndoS49 polypeptide which is derivatised or modified as described above.

Preferably, step (a) of the above method additionally comprises contacting the sample with a population of magnetic nanoparticles capable of binding to IdeS, step (c) additionally comprises contacting the Fab and Fc fragments obtained in step (b) with a population of magnetic nanoparticles capable of binding to the EndoS49 polypeptide, and wherein steps (b) and (d) comprise carrying out magnetic field separation on the sample of (a) and mixture obtained in (c), respectively. The EndoS49 polypeptide is preferably a modified EndoS49 polypeptide lacking endoglycosidase activity.

In an alternative embodiment, Fc fragments may be isolated from an IgG-containing sample by a method comprising:
(a) contacting said IgG-containing sample with IdeS and an EndoS49 polypeptide
(b) separating the EndoS49 polypeptide from the mixture obtained in (a);
thereby isolating Fc fragments.

It will be understood that any suitable separation means may be used as described above. However, preferably step (a) of the above method additionally comprises contacting the sample with a population of magnetic nanoparticles capable of binding to the EndoS49 polypeptide but not to IdeS, and wherein step (b) comprises carrying out magnetic field separation on the mixture obtained in (a). Preferably, the IdeS and/or the EndoS49 polypeptide are derivatised or modified as described above, with the proviso that a different modification is applied to each. For example, where the IdeS is modified by addition of a histidine tag such that it binds to a population of magnetic particles containing on their surface chelating groups which carry a nickel, copper or zinc ion, the EndoS49 polypeptide might be modified by addition of a biotin tag such that it binds to a population of magnetic particles containing on their surface streptavidin. The EndoS49 polypeptide is preferably a modified EndoS49 polypeptide lacking endoglycosidase activity.

Similar to the methods for isolating Fab fragments, it will be appreciated that in the methods for separating Fc fragments the IgG-containing sample typically comprises purified or isolated IgG. A preferred method of isolating IgG is described in steps (i) to (iii) as set out above.

Kits

The Present Invention Provides
a kit for isolating IgG from an IgG-containing sample, comprising:
(a) an EndoS49 polypeptide according to the invention which lacks endoglycosidase activity; and optionally
(b) means for separating said EndoS49 polypeptide from a sample.
a kit for determining the presence or absence of IgG in a sample, comprising:
(a) an EndoS49 polypeptide according to the invention which lacks endoglycosidase activity; and optionally
(b) means for separating said EndoS49 polypeptide from a sample.
a kit for assessing the glycosylation state and/or functional quality of an IgG containing sample, comprising:
(a) an EndoS49 polypeptide according to the invention which lacks endoglycosidase activity; and optionally;
(b) an alternative IgG-binding reagent which is capable of binding denatured and/or deglycosylated IgG;
(c) means for separating said EndoS49 polypeptide from a sample; and
(d) means for separating said alternative IgG-binding reagent from a sample.

The alternative IgG-binding reagent comprises Protein G and/or Protein A and/or Protein A/G.

The present invention also provides:
a kit for isolating Fab or Fc fragments of IgG comprising:
(a) IdeS;
(b) an EndoS49 polypeptide; and
(c) means for separating said IdeS and said EndoS49 polypeptide from a sample.

In a preferred embodiment, the kit additionally comprises an EndoS49 polypeptide according to the invention which lacks endoglycosidase activity and a means for separating said EndoS49 polypeptide from a sample. The EndoS49 polypeptide is preferably an EndoS49 polypeptide according to the invention which lacks endoglycosidase activity.

Preferred embodiments of the above kits further comprise instructions for using the kit in a method of the invention. Further preferred embodiments include those wherein the means for separating an EndoS49 polypeptide, an alternative IgG-binding reagent, an IdeS polypeptide, or an EndoS49 polypeptide from a sample are populations of magnetic nanoparticles, wherein each population is capable of binding to at least one of the indicated polypeptides/reagents/proteins. In this embodiment the kit typically additionally comprises instructions to perform magnetic field separation on the sample.

In preferred embodiments of the above methods and kits, the polypeptides/proteins/reagents used are derivatised with an affinity tag, preferably a histidine tag, to assist with separation of said polypeptides.

The Following Examples Illustrate the Invention

EXAMPLE 1

Materials and Methods
Bacterial Strains and Growth

The genome of GAS strain NZ131 of serotype M49 has been sequenced and this strain was therefore selected as reference strain in this work (McShan et al., 2008) (Chaussee et al., 1999). GAS strain NZ131 was propagated on blood agar and *Escherichia coli* strains Top10 (Invitrogen) and BL21 pLysS (Invitrogen) were propagated on lysogeny broth (LB) agar. For selection in *E. coli* Top10 cells, carbenicillin was used at 100 μg/mL and for *E. coli* BL21 pLysS, 100 μg/mL carbenicillin and 34 μg/mL chloramphenicol were used. Overnight cultures of *E. coli* were carried out in LB at 37° C. with aeration. Genomic DNA preparation of GAS strain NZ131 was performed using Puregene DNA Purification Kit (Qiagen). Transformation was carried out using heat-shock at 42° C. for 30 s. Plasmid preparations from *E. coli* were performed using Plasmid Miniprep Kit I (E.Z.N.A). All primers used in this work are listed in Table 2.

Recombinant Expression of EndoS49

Recombinant expression of EndoS49 in *E. coli* was established by PCR amplification of the ndoS49 gene from group A *Streptococcus* strain NZ131, serotype M49 with the primers ndoS49-F-BamHI, CTGTAA GGATCCAGGAGAAGACTG, and ndoS49-R-XhoI, GAAACCTCGAGTCTTTGTAATCGTAGGACTT. The ndoS49 gene fragment was digested with restriction enzymes BamHI and XhoI and ligated into the expression vector pGEX-5X-3 (Amersham Biosciences) using DNA ligase T4 (Fermentas) creating the plasmid pGEX-ndoS49. The expression vector was transformed into *E. coli* Top 10 chemically competent cells and recombinant cells were grown on 100 μg/mL carbenicillin plates and screened with PCR using primers ndoS49-F-BamHI and ndoS49-R-XhoI. Positive clones were isolated and the pGEX-ndoS49 plasmid was purified and transformed into the *E. coli* expression strain BL21 pLysS as described above.

One recombinant clone was grown overnight at 37° C. with antibiotics and diluted 1:20 in LB medium with antibiotics and grown for 3 h. The expression of the protein EndoS49 was induced with 0.1 mM IPTG for 3 h. The cells were harvested and lysed with BugBuster Protein Extraction Reagent (Novagen). Recombinant GST-EndoS49 was purified on column with Glutathione Sepharose 4B (GE Healthcare) and eluated with reduced glutathione.

Mutagenesis of EndoS49

Site-directed mutagenesis of the glutamic acid 186(Glu-186) to leucine (E186L) was carried out using QuickChange II Site-Directed Mutagenesis Kit (Stratagene) according to the manufacturer's instructions. The mutagenesis primer used was CTAGATATTGATATT CTTCACGAATTTACGAAC in combination with the anti-sense of the sequence above and the plasmid pGEX-ndoS49 (mutation underlined). This generated the plasmids pGEX-ndoS49(E186L) and, after sequencing, recombinant EndoS49(E186L) was expressed and purified as described for EndoS49. The truncated versions of EndoS49 were constructed by amplifying parts of the ndoS49 gene from GAS NZ131 with primersndoS49(trunc1-5) containing restrictions sites BamHI and XhoI (Table 2). The fragments were digested and ligated into the pGEX vector as above, and transformed into *E. coli* Top10 and subsequently to BL21 pLysS and grown with antibiotics. The proteins were produced as above and the proteins EndoS49(trunc1) 80 kDa, EndoS49(trunc2) 70 kDa, EndoS49(trunc3) 60 kDa, EndoS49(trunc4) 50 kDa, EndoS49(trunc5) 42 kDa were purified.

Glycoprotein Glycan Hydrolysis Assay

1 μg recombinant EndoS49 and its mutants were incubated with 3 μg of each glycoprotein in 20 μL PBS overnight at 37° C. Glycan hydrolysis was analyzed on a 10% SDS-PAGE gel and subsequently analyzed with LCA lectin blot as previously described (Collin and Olsen, 2001a).

Slot-blot Analysis

EndoS49 and its mutants were immobilized on a methanol activated PVDF membrane at 4, 2, 1 μg in PBS per slot using Millipore slot blot equipment. The membrane was blocked with 5% skim milk (Difco) for 1 h at room temperature. Washing was consistently carried out for 3×10 minutes in PBST. The membrane was incubated with 10 μg human IgG (Sigma) in 0.5% skim milk for 1 h at 37° C. and then washed. 5 μg horseradish peroxidase conjugated with protein G (Invitrogen) was added to the membrane and incubated for 1 h at 37° C. After washing the membrane was developed with Supersignal West Pico Chemiluminiscent Substrate (Thermo Scientific).

Bioinformatic Analysis

The genes ndoS49 and ndoS were translated into EndoS49 and EndoS and compared using the ClustalW algorithmin within the software MacVector (MacVector Inc.). The phylogenetic tree was constructed with MacVector using protein sequences from NCBI PubMed with the following accession numbers: EndoS (AF296340), EndoE (AAR20477), EndoH (NP_631673), EndoC (ADC53484), EndoF2 (P36912), EndoF3 (P36913) (Collin and Olsén, 2001b) (Collin and Fischetti, 2004) (Tarentino and Plummer, 1974) (Tarentino et al., 1993).

PCR Screening for ndoS49

Primers amplifying the ndoS49 gene from GAS were designed and denoted ndoS49-F (AAAACGCGGACCAC-TATATGC) and ndoS49-R (AAACGTTGTCCGAG-GATTTG). 42 GAS strains were propagated on blood agar and grown overnight at 37° C. with 5% $CO_2$. Single colonies were picked and lysed in 20 μL sterile $H_2O$ at 99° C. for 10 minutes. These lysates were used as template for a stringent PCR reaction to detect ndoS49 in the 42 GAS strains. As a positive control, primers for the amplification of the gene recA were designed, recA-F (AGCCCTTGATGAT-GCTTTG) and recA-R (AACAATTCTGGGTGATCGG). As positive controls, both PCR reactions used genomic DNA from GAS strain NZ131 (M49) and AP1 (M1) as template.

Results

ClustalW Analysis Reveals Two Different Enzymes: EndoS49 and EndoS

Figure 1:
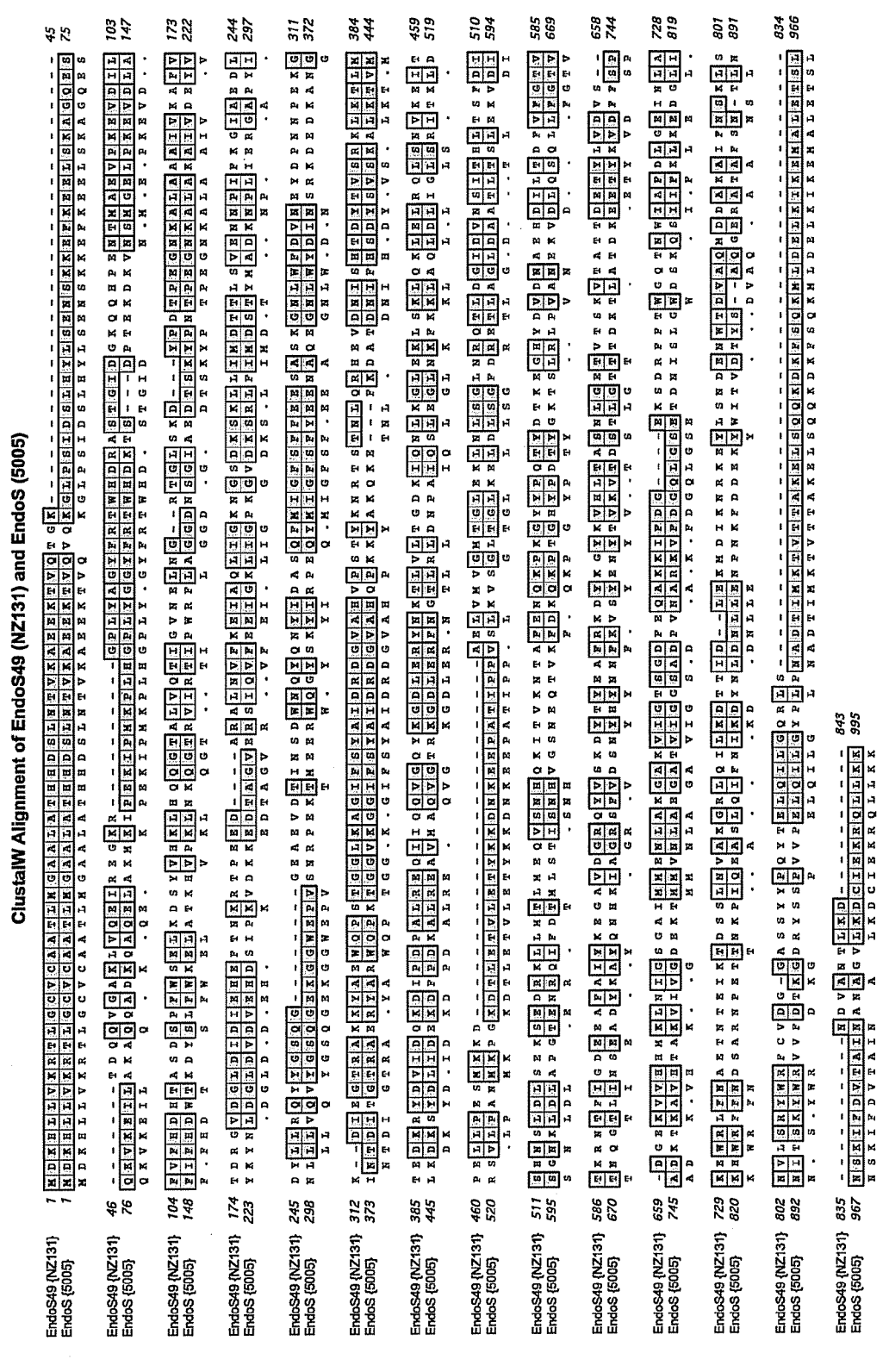

The genes ndoS49 and ndoS were in silico translated into proteins and compared using the ClustalWalgorithm. On the gene level the identity is 50% and 37% on the protein level. The ClustalW analysis revealed a (nearly) identical signal peptide sequence and a conserved family 18 glycoside hydrolasecatalytic domain (DGLDIDIE)(FIG. 1). Experimental analysis of EndoS has shown that tryptophans are essential for the glycan-hydrolyzing activity (Allhorn et al., 2008). These tryptophans are also conserved in EndoS49.

Recombinant EndoS49 Show Glycan Hydrolyzing Activity on Human Glycoproteins

The 90 kDa EndoS49 was successfully recombinantly expressed in *E. coli* BL21 and purified from the soluble fraction using the GST-tag. EndoS49(E186L), a catalytic mutant with the glutamic acid of the GH18 motif (E186) substituted for a leucine (L), was constructed and purified in the same way. To map the activity of the protein, 5 carboxy-terminally truncated versions of the enzymes were constructed and denoted EndoS49(trunc1) 80 kDa, EndoS49 (trunc2) 70 kDa, EndoS49(trunc3) 60 kDa, EndoS49 (trunc4) 50 kDa and EndoS49(trunc5) 42 kDa. This collection of enzymes was utilized to analyze the glycan hydrolyzing activity of EndoS49 on human glycoproteins. First, the enzymes were incubated with human IgG overnight and analyzed on a SDS-PAGE gel and with LCA lectin blot, detecting the mannose structures in the glycan of IgG. The gel revealed a shift of 4 kDa of the IgG heavy chain treated with EndoS49 and the LCA lectin blot confirmed this shift as a lack of the N-linked glycan (FIG. 2A). EndoS49 (E186L) showed no shift and no change in glycan composition suggesting that E186 plays a crucial role in the catalytic activity of EndoS49. Concerning the truncated enzymes, EndoS49(trunc1-4) showed activity on the glycan of IgG but EndoS49(trunc5), the smallest of the enzymes (42 kDa), showed no glycan-hydrolyzing activity (FIG. 2A).

Further analysis of the IgG deglycosylation by EndoS49 was carried out by incubating $IgG_{1-4}$ with EndoS49 and EndoS49(E186L), overnight. The IgG subclasses were analyzed as above and showed that EndoS49 has activity on all four subclasses of IgG, and in line with previous result, the catalytic mutant showed no activity (FIG. 2B). Incubating the collection of enzymes with alpha-1-microglobulin, a heavy glycosylated human serum protein, and analysis on SDS-PAGE showed glycan hydrolysis activity of EndoS49 on this glycoprotein (FIG. 2C). To further elucidate the specificity of EndoS49, a model substrate consisting of a N-acetyl-beta-D-glucosaminide coupled to the fluorescent 4-methylumbelliferyl was incubated with EndoS49 for 1, 2, 3, 4 and 16 h and the fluorescence measured. The fluorescence will increase if the sugar is cleaved but no such increase in intensity was observed (data not shown) suggesting that EndoS49 has activity only on glycoprotein substrates.

EndoS49 Binding to IgG

The finding that EndoS49 has glycan hydrolyzing activity on IgG led us to believe that the enzyme binds IgG. This was evaluated with slot blot analysis where EndoS49 and its catalytic mutant and truncated versions were immobilized on a PVDF membrane and incubated with IgG and the binding detected with protein G coupled to Horseradish-peroxidase (HRP). The slot blot show an increased binding to IgG by the catalytic mutant EndoS49(E186L) (FIG. 3).

The Gene ndoS49 is Present in GAS Serotype M49

To elucidate whether ndoS49 is present in any other serotypes than M49 a stringent PCR was deployed to analyze the presence of the ndoS49 gene in a selection of GAS strains. The primers ndoS49-F and ndoS49-R was used in a PCR on lysates from GAS colonies together with the positive control amplifying the recA gene, present in all GAS strains. The ndoS49 gene was amplified in all selected GAS M49 serotypes and also in serotype M60, whereas no other serotype gave a PCR product (Table 1).

Figure 4:
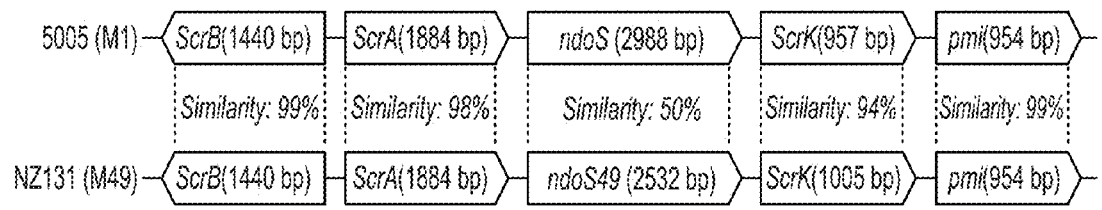
FIG. 4. The genomic context of ndoS49 and ndoS. A comparison of the genes surrounding ndoS49 and ndoS in GAS strains NZ131 (M49) and 5005 (M1) was carried out in MacVector.

In the sequenced genomes of GAS strains NZ131 (M49) and MGAS5005 (M1) the genes surrounding ndoS49 and ndoS were compared revealing that the genes are located in the same genomic context and that the surrounding genes are highly conserved (FIG. 4). The full length EndoS49 was compared to a selection of previously described endoglycosidases, EndoS, EndoC, EndoH, EndoE, EndoF2, EndoF3) and a phylogenetic tree was reconstructed (FIG. 5). This revealed that EndoS and EndoC are more closely related than EndoS and EndoS49 and that endoglycosidases from *Streptococcus* are close related compared to enzymes from other bacteria.

TABLE 1

The presence of ndoS49 in a selection of GAS serotypes

| Strain | Serotype | ndoS49 | recA |
|---|---|---|---|
| 5448 | M1 | − | + |
| SF370 | M1 | − | + |
| ACN1 | M1 | − | + |
| ACN2 | M2 | − | + |
| ANC3 | M3 | − | + |
| 20224 | M3 | − | + |
| ACN4 | M4 | − | + |
| ACN5 | M5 | − | + |
| Manfredo | M5 | − | + |
| ACN6 | M6 | − | + |
| AP6 | M6 | − | + |
| ACN9 | M9 | − | + |
| ACN11 | M11 | − | + |
| ACN12 | M12 | − | + |
| ACN18 | M18 | − | + |
| ACN19 | M19 | − | + |
| ACN22 | M22 | − | + |
| ACN24 | M24 | − | + |
| ACN28 | M28 | − | + |
| NZ131 | M49 | + | + |
| 3487-05 | M49 | + | + |
| AW1 | M49 | + | + |
| AW2 | M49 | + | + |
| AW3 | M49 | + | + |
| AW4 | M49 | + | + |
| AW6 | M49 | + | + |
| AW7 | M49 | + | + |
| AW8 | M49 | + | + |
| AW9 | M49 | + | + |
| AW10 | M49 | + | + |
| AW11 | M49 | + | + |
| AW12 | M49 | + | + |
| AW13 | M49 | + | + |
| ACN49 | M49 | + | + |
| AP49 | M49 | + | + |
| CS101 | M49 | + | + |
| AP53 | M53 | − | + |
| ALAB49 | M53 | − | + |
| ACN55 | M55 | − | + |
| ACN57 | M57 | − | + |
| ACN60 | M60 | + | + |
| AP74 | M74 | − | + |

TABLE 2

Primers used in this work

| Primer name | Sequence (5'-3') |
|---|---|
| ndoS49-F-BamHI | CTGTAAGGATCCAGGAGAAGACTG |
| ndoS49-R-XhoI | GAAACCTCGAGTCTTTGTAATCGTAGGACTT |
| ndoS49 (E186L)-F | CTAGATATTGATATTCTTCACGAATTTACGAAC |
| ndoS49 (E186L)-R | GTTCGTAAATTCGTGAAGAATATCAATATCTAG |
| ndoS49 (trunc1)-R-XhoI | ATTTCTCGAGCTGAAGACGTCCTTTAGCCACG |
| ndoS49 (trunc2)-R-XhoI | TAAACTCGAGCCCCATCAGAAACATCTACTAAG |
| ndoS49 (trunc3)-R-XhoI | ATTTTCTCGAGGCATTATCAACATCATAATGACC |
| ndoS49 (trunc4)-R-XhoI | TAAACTCGAGCCAGTCATGCCTACCATAACAAGCTCAGC |

TABLE 2-continued

Primers used in this work

| Primer name | Sequence (5'-3') |
|---|---|
| ndoS49 (trunc5)-R-XhoI | ATTTCTCGAGCTGTCCAACTTGTTGAATG |
| ndoS49-F | AAAACGCGGACCACTATATGC |
| ndoS49-R | AAACGTTGTCCGAGGATTTG |
| recA-F | AGCCCTTGATGATGCTTTG |
| recA-R | AACAATTCTGGGTGATCGG |

The Protein Sequence of EndoS49
NCBIReferenceSequences
NZ131 genome: NC_011375.1
ndoS49 gene sequence: NC_011375.1
EndoS49 protein sequence: YP_002286383.1

```
EndoS49 Protein Sequence:
MDKHLLVKRTLGCVCAATLMGAALATHHDSLNTVKAEEKTVQTG

KTDQQVGAKLVQEIREGKRGPLYAGYFRTWHDRASTGIDGKQQH

PENTMAEVPKEVDILFVFHDHTASDSPFWSELKDSYVHKLHQQG

TALVQTIGVNELNGRTGLSKDYPDTPEGNKALAAAIVKAFVTDR

GVDGLDIDIEHEFTNKRTPEEDARALNVFKEIAQLIGKNGSDKS

KLLIMDTTLSVENNPIFKGIAEDLDYLLRQYYGSQGGEAEVDTI

NSDWNQYQNYIDASQFMIGFSFFEESASKGNLWFDVNEYDPNNP

EKGKDIEGTRAKKYAEWQPSTGGLKAGIFSYAIDRDGVAHVPST

YKNRTSTNLQRHEVDNISHTDYTVSRKLKTLMTEDKRYDVIDQK

DIPDPALREQIIQQVGQYKGDLERYNKTLVLTGDKIQNLKGLEK

LSKLQKLELRQLSNVKEITPELLPESMKKDAELVMVGMTGLEKL

NLSGLNRQTLDGIDVNSITHLTSFDISHNSLDLSEKSEDRKLLM

TLMEQVSNHQKITVKNTAFENQKPKGYYPQTYDTKEGHYDVDNA

EHDILTDFVFGTVTKRNTFIGDEEAFAIYKEGAVDGRQYVSKDY

TYEAFRKDYKGYKVHLTASNLGETVTSKVTATTDETYLVDVSDG

EKVVHHMKLNIGSGAIMMENLAKGAKVIGTSGDFEQAKKIFDGE

KSDRFFTWGQTNWIAFDLGEINLAKEWRLFNAETNTEIKTDSSL

NVAKGRLQILKDTTIDLEKMDIKNRKEYLSNDENWTDVAQMDDA

KAIFNSKLSNVLSRYWRFCVDGGASSYYPQYTELQILGQRLSND

VANTLKD
```

EXAMPLE 2

Monoclonal Ig molecules can show minor variations in the Fc glycans and as a consequence the Fc glycans can appear as an inhomogeneous pool of Fc glycans. The vast majority of the glycans are identical but a minority can show variable carbohydrate structure or composition. The variety arises both from the origin of the Fc part, which can be human, humanized or from another species, and from the choice of production cell-line and cell culture conditions. In this example two well-known IgG based drugs, Avastin and Erbitux, were deglycosylated both with EndoS and with EndoS49. The samples were incubated with EndoS or EndoS49 as set out in the Table below.

| Lane | Sample | Erbitux 100 µg | Avastin 100 µg | EndoS 0.1 mg/ml (µl) | EndoS49 0.1 mg/ml (µl) | ideS 1 µg |
|---|---|---|---|---|---|---|
| 1 | MW standard | − | − | — | — | − |
| 2 | | − | + | 5 | — | + |
| 3 | | − | + | 50 | — | + |
| 4 | | − | + | — | 5 | + |
| 5 | | − | + | — | 50 | + |
| 6 | | − | + | — | — | + |
| 7 | | + | − | 5 | — | + |
| 8 | | + | − | 50 | — | + |
| 9 | | + | − | — | 5 | + |
| 10 | | + | − | — | 50 | + |
| 11 | | + | − | — | — | + |
| 12 | MW standard | − | − | — | — | − |

The results are presented in FIG. 6. It was found that EndoS49 has the potential to cleave a larger variety of Fc glycans than EndoS. Even if incubation was left over night in order to minimize the effect of potential differences in the enzymatic activities the EndoS enzyme could not fully deglycosylate Erbtux Fc glycans. However EndoS49 shows a complete deglycosylation profile and is hence the more favourable enzyme when it comes to glycan profiling of immunoglobulins.

The invention claimed is:

1. A method for completely deglycosylating an immunoglobulin comprising incubating the immunoglobulin with a polypeptide comprising:
   (a) the amino acid sequence of SEQ ID NO:1; or
   (b) a variant thereof having at least 95% identity to the amino acid sequence of SEQ ID NO:1 over at least 810 contiguous amino acids and having the endoglycosidase activity of a polypeptide consisting of the amino acid sequence of SEQ ID NO:1.

2. The method of claim 1, further comprising assessing the glycosylation profile of said immunoglobulin by
   (a) separating glycan from the deglycosylated immunoglobulin; and
   (b) analysing the glycan and/or deglycosylated immunoglobulin so produced.

3. The method of claim 1, wherein the immunoglobulin comprises an IgG antibody or Fc fragment thereof.

* * * * *